(12) United States Patent
DePinho et al.

(10) Patent No.: US 10,378,060 B2
(45) Date of Patent: Aug. 13, 2019

(54) ZNF365/ZFP365 BIOMARKER PREDICTIVE OF ANTI-CANCER RESPONSE

(71) Applicant: Dana-Farber Cancer Institute, Inc., Boston, MA (US)

(72) Inventors: Ronald A. DePinho, Houston, TX (US); Ji-Hye Paik, New York, NY (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 358 days.

(21) Appl. No.: 14/350,164

(22) PCT Filed: Oct. 11, 2012

(86) PCT No.: PCT/US2012/059738
§ 371 (c)(1),
(2) Date: Apr. 7, 2014

(87) PCT Pub. No.: WO2013/055911
PCT Pub. Date: Apr. 18, 2013

(65) Prior Publication Data
US 2014/0235686 A1  Aug. 21, 2014

Related U.S. Application Data

(60) Provisional application No. 61/547,212, filed on Oct. 14, 2011.

(51) Int. Cl.
*C12Q 1/6886* (2018.01)
*G01N 33/574* (2006.01)
*A61N 5/10* (2006.01)
*A61K 31/4184* (2006.01)

(52) U.S. Cl.
CPC ........ *C12Q 1/6886* (2013.01); *A61K 31/4184* (2013.01); *A61N 5/10* (2013.01); *G01N 33/57496* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2009/0068684 A1 | 3/2009 | Moritz et al. |
| 2009/0163435 A1 | 6/2009 | Bader et al. |
| 2009/0175827 A1 | 7/2009 | Byrom et al. |
| 2009/0227533 A1 | 9/2009 | Bader et al. |
| 2009/0232893 A1 | 9/2009 | Bader et al. |
| 2009/0325189 A1 | 12/2009 | Hornbeck et al. |
| 2010/0130527 A1 | 5/2010 | Lehrer et al. |
| 2010/0196426 A1 | 8/2010 | Skog et al. |

FOREIGN PATENT DOCUMENTS

| | | |
|---|---|---|
| EP | 1975184 A2 | 10/2008 |
| GB | 2444410 A | 6/2008 |
| WO | WO-2004/035828 A2 | 4/2004 |
| WO | WO-2007/064776 A2 | 6/2007 |
| WO | WO-2007/122369 A2 | 11/2007 |
| WO | WO-2008/036718 A2 | 3/2008 |
| WO | WO-2008/036741 A2 | 3/2008 |
| WO | WO-2008/073923 A2 | 6/2008 |
| WO | WO-2008/082730 A2 | 7/2008 |
| WO | WO-2008/085797 A2 | 7/2008 |
| WO | WO-2008/144345 A2 | 11/2008 |
| WO | WO-2008/154333 A2 | 12/2008 |
| WO | WO-2009/100029 A1 | 8/2009 |
| WO | WO-2009/108917 A2 | 9/2009 |
| WO | WO-2009/117122 A2 | 9/2009 |
| WO | WO-2010/065940 A1 | 6/2010 |
| WO | WO-2010/088688 A2 | 8/2010 |
| WO | WO-2011/088237 A1 | 7/2011 |

OTHER PUBLICATIONS

Yoshino (International Journal of Oncology 2010 vol. 36 pp. 1367-1377).*
Dhawan (Current Opinion in Molecular Therapeutics 2009 11(6) 670-680).*
Dermer (Biotechnology 1994 vol. 12 p. 320).*
Tsuji (BMC Cancer 2010 vol. 10 No. 15 pp. 1-10).*
Beroukhim (Nature vol. 463 No. 18 Feb. 2010 pp. 899-905).*
Egan (Nature Genetics vol. 39 No. 11 Nov. 2007 pp. 1384-1388).*
Zhang (DNA Copy Number Profiling in Normal and Tumor Genomes found online at http://statweb.stanford.edu/~nzhang/zhang_qmpbook.pdf and viewed Nov. 29, 2016).*
Evers (Clin Cancer Res 2008 vol. 14 No. 12 Jun. 15, 2008 pp. 3916-3925).*
Tutt (Lancet 2010 376 pp. 235-244).*
Antoniou et al., "Common variants at 12p11, 12q24, 9p21, 9q31.2, and in ZNF365 are associated with breast cancer risk for BRCA1 and/or BRCA2 mutation carriers," Breast Cancer Research, 14:R33 (2012).
Chen et al., "MicroRNA-193B Represses Cell Proliferation and Regulates Cyclin D1 in Melanoma," The American Journal of Pathology, 176(5):2520-2529 (2010).
Gaudet et al., "Common Genetic Variants and Modification of Penetrance of BRCA2-Associated Breast Cancer," PloS Genetics, 6(10):e1001183 (2010).
Gianfrancesco et al., "Identification of a Novel Gene and a Common Variant Associated with Uric Acid Nephrolithiasis in a Sardinian Genetic Isolate," Am. J. Hum. Genet., 72:1479-1491 (2003).
Gianfrancesco et al., "Emergence of Talanin protein associated with human uric acid nephrolithiasis in the Hominidae lineage," Gene, 339:131-138 (2004).
Lindstrom et al., "Common variants in ZNF365 are associated with both mammographic density and breast cancer risk," Nature Genetics, 43:185-187 (2011).
Turnbull et al., "Genome-wide association study identifies five new breast cancer susceptibility loci," Nature Genetics, 42(6):504-507 (2010).
Yoshino et al., "Gene expression profiling predicts response to temozolomide in malignant gliomas," International Journal of Oncology, 36:1367-1377 (2010).
International Search Report dated Mar. 8, 2013, from PCT/US2012/059738.

* cited by examiner

*Primary Examiner* — Amanda Haney
(74) *Attorney, Agent, or Firm* — Foley Hoag LLP

(57) ABSTRACT

The present invention is based on the identification of novel biomarkers predictive of response to anti-cancer therapies.

9 Claims, 15 Drawing Sheets

Specification includes a Sequence Listing.

| symbol | p-value | Fold | amp | del | link to p53 |
|---|---|---|---|---|---|
| Phlda3 | 5E-07 | 5.33975 | 0 | 1 | known |
| Gdf15 | 6E-06 | 2.29579 | 1 | 1 | known |
| Zfp365 | 4E-05 | 4.77261 | 3 | 0 | |
| Ckap2 | 1E-04 | 2.56015 | 0 | 3 | known |
| Mdm2 | 1E-04 | 8.61567 | 3 | 0 | known |
| Pmaip1 | 0.0004 | 14.1756 | na | na | known |
| Cdkn1a | 0.0009 | 8.32956 | 0 | 1 | known |
| Arhgef4 | 0.0011 | 5.14391 | 0 | 1 | |
| Rap2b | 0.0012 | 1.80614 | 1 | 0 | |
| Eda2r | 0.0019 | 10.1114 | 0 | 0 | |
| Gtse1 | 0.0022 | 1.77269 | 3 | 2 | known |
| Anxa8 | 0.0028 | 2.01822 | na | na | |
| Btg2 | 0.0035 | 2.96356 | 1 | 0 | known |
| Tmem19 | 0.0038 | 2.43134 | 0 | 2 | |
| Trp53inp1 | 0.0046 | 11.1339 | 2 | 1 | known |
| Pard6g | 0.0047 | 1.96886 | 4 | 2 | |
| Ccng1 | 0.0049 | 5.30906 | 0 | 1 | known |
| Trim11 | 0.0055 | 1.7069 | 1 | 2 | |
| Sesn2 | 0.0064 | 1.69595 | 0 | 1 | known |
| Evpl | 0.0074 | 4.26354 | 1 | 1 | |
| Matn4 | 0.0075 | 2.60503 | 0 | 2 | |
| Scmh1 | 0.008 | 1.94042 | 0 | 2 | |
| Mxd4 | 0.0093 | 1.86929 | 1 | 1 | |
| Slc19a2 | 0.0097 | 1.82838 | 1 | 1 | |
| Mapkapk3 | 0.0118 | 2.38004 | 0 | 3 | |
| Perp | 0.0163 | 2.23466 | 0 | 1 | known |

Top-ranked genes induced upon p53 activation in cells with telomere-dysfunction and genomic instability p-value < 0.001  7 genes p-value < 0.01  24 genes
p-value < 0.1 ~ 56 genes

SEQUENCE LISTING

```
<160> NUMBER OF SEQ ID NOS: 11

<210> SEQ ID NO 1
<211> LENGTH: 1224
<212> TYPE: DNA
<213> ORGANISM: Homo sapiens

<400> SEQUENCE: 1
atgcaacaga aggcttttga ggaaagcaga tatccctggc aggagtcctt tgagaatgtt      60
gctgtgtgcc tgccattacg ctgcccgagg tgtggagacc ataccagatt tagaagcttg     120
tcatccttga gggcccatct ggagttcagt cacagctacg aagaaagaac cctcttgaca     180
aaatgcagtc tctttccatc cctcaaagac acagacctag tcacttcctc agaactcctg     240
aaaccgggaa aattgcagag cagtggcaac gtggtaaagc agaaaccgag ctatgttaac     300
ttgtacagca tttcacatga acattccaag gacaggaagc catttgaggt ggtggcagag     360
aggcctgtgt cctatgtgca gacctacact gccatggacc tccatgcaga ctcgctggat     420
gggacacggt cgggtcctgg actgcccacc tcagacacca aagcttcttt cgaggcacat     480
gtcagagaaa aattcaatcg aatggttgag gctgtggata ggaccattga aagagaatt      540 gataaactca ccaaagagtt ggcccagaaa actgcggaac tgttggaagt tcgggcagct     600
tttgtgcagc tgactcagaa aaagcaggaa gttcagagac gagagcgggc cttaaacaga     660
caggtggacg tggccgtgga aatgatagct gtactgaggc aacgcctgac ggaatctgag     720
gaggagcttc ttaggaaaga agaagaagtt gtcacattca accatttcct ggaagcggca     780
gctgagaagg aggttcaagg gaaagcccgg ctccaggact ttattgagaa tctgttacag     840
cgggtagaac tggcggagaa gcagcttgag tactatcaga gccagcaggc ctctggcttt     900
gtccgtgatc tcagcgggca cgtgcttaca gacatctcct caaataggaa gcccaaatgc     960
ctaagccgag ggcacccgca ttcggtatgt aaccaccctg atctcaaggc ccatttccac    1020
ccaaagggaa ggaaccacct gaaaaaggcc aaggatgaca gagccagcat gcagcctgcc    1080
```

```
aaggccattc acgaacaggc tgagtcctca agagacctct gcagacctcc aaagaaaggg   1140
gagctcctgg ggtttggccg caaaggcaac atcaggccca aaatggctaa aaaaaagcca   1200
acagccattg tgaacatcat ctaa                                          1224
```

<210> SEQ ID NO 2
<211> LENGTH: 407
<212> TYPE: PRT
<213> ORGANISM: Homo sapiens

<400> SEQUENCE: 2

```
Met Gln Gln Lys Ala Phe Glu Glu Ser Arg Tyr Pro Trp Gln Glu Ser
1               5                   10                  15

Phe Glu Asn Val Ala Val Cys Leu Pro Leu Arg Cys Pro Arg Cys Gly
                20                  25                  30

Asp His Thr Arg Phe Arg Ser Leu Ser Ser Leu Arg Ala His Leu Glu
            35                  40                  45

Phe Ser His Ser Tyr Glu Glu Arg Thr Leu Leu Thr Lys Cys Ser Leu
        50                  55                  60

Phe Pro Ser Leu Lys Asp Thr Asp Leu Val Thr Ser Ser Glu Leu Leu
65                  70                  75                  80

Lys Pro Gly Lys Leu Gln Ser Ser Gly Asn Val Val Lys Gln Lys Pro
                85                  90                  95

Ser Tyr Val Asn Leu Tyr Ser Ile Ser His Glu His Ser Lys Asp Arg
            100                 105                 110

Lys Pro Phe Glu Val Val Ala Glu Arg Pro Val Ser Tyr Val Gln Thr
        115                 120                 125

Tyr Thr Ala Met Asp Leu His Ala Asp Ser Leu Asp Gly Thr Arg Ser
130                 135                 140

Gly Pro Gly Leu Pro Thr Ser Asp Thr Lys Ala Ser Phe Glu Ala His
145                 150                 155                 160

Val Arg Glu Lys Phe Asn Arg Met Val Glu Ala Val Asp Arg Thr Ile
                165                 170                 175

Glu Lys Arg Ile Asp Lys Leu Thr Lys Glu Leu Ala Gln Lys Thr Ala
            180                 185                 190

Glu Leu Leu Glu Val Arg Ala Ala Phe Val Gln Leu Thr Gln Lys Lys
        195                 200                 205

Gln Glu Val Gln Arg Arg Glu Arg Ala Leu Asn Arg Gln Val Asp Val
    210                 215                 220

Ala Val Glu Met Ile Ala Val Leu Arg Gln Arg Leu Thr Glu Ser Glu
225                 230                 235                 240

Glu Glu Leu Leu Arg Lys Glu Glu Val Val Thr Phe Asn His Phe
                245                 250                 255

Leu Glu Ala Ala Ala Glu Lys Glu Val Gln Gly Lys Ala Arg Leu Gln
            260                 265                 270

Asp Phe Ile Glu Asn Leu Leu Gln Arg Val Glu Leu Ala Glu Lys Gln
        275                 280                 285

Leu Glu Tyr Tyr Gln Ser Gln Gln Ala Ser Gly Phe Val Arg Asp Leu
    290                 295                 300

Ser Gly His Val Leu Thr Asp Ile Ser Ser Asn Arg Lys Pro Lys Cys
305                 310                 315                 320

Leu Ser Arg Gly His Pro His Ser Val Cys Asn His Pro Asp Leu Lys
                325                 330                 335

Ala His Phe His Pro Lys Gly Arg Asn His Leu Lys Lys Ala Lys Asp
            340                 345                 350
```

Asp Arg Ala Ser Met Gln Pro Ala Lys Ala Ile His Glu Gln Ala Glu
            355                 360                 365

Ser Ser Arg Asp Leu Cys Arg Pro Pro Lys Lys Gly Glu Leu Leu Gly
        370                 375                 380

Phe Gly Arg Lys Gly Asn Ile Arg Pro Lys Met Ala Lys Lys Pro
385                 390                 395                 400

Thr Ala Ile Val Asn Ile Ile
                405

<210> SEQ ID NO 3
<211> LENGTH: 1002
<212> TYPE: DNA
<213> ORGANISM: Homo sapiens

<400> SEQUENCE: 3

```
atgcaacaga aggcttttga ggaaagcaga tatccctggc aggagtcctt tgagaatgtt    60
gctgtgtgcc tgccattacg ctgcccgagg tgtggagacc ataccagatt tagaagcttg   120
tcatccttga gggcccatct ggagttcagt cacagctacg aagaaagaac cctcttgaca   180
aaatgcagtc tctttccatc cctcaaagac acagacctag tcacttcctc agaactcctg   240
aaaccgggaa aattgcagag cagtggcaac gtggtaaagc agaaaccgag ctatgttaac   300
ttgtacagca tttcacatga acattccaag gacaggaagc catttgaggt ggtggcagag   360
aggcctgtgt cctatgtgca gacctacact gccatggacc tccatgcaga ctcgctggat   420
gggacacggt cgggtcctgg actgccacc tcagacacca agcttctttt cgaggcacat   480
gtcagagaaa aattcaatcg aatggttgag gctgtggata ggaccattga aagagaatt   540
gataaactca ccaaagagtt ggcccagaaa actgcggaac tgttggaagt tcgggcagct   600
tttgtgcagc tgactcagaa aaagcaggaa gttcagagac gagagcgggc cttaaacaga   660
caggtggacg tggccgtgga aatgatagct gtactgaggc aacgcctgac ggaatctgag   720
gaggagcttc ttaggaaaga agaagaagtt gtcacattca accatttcct ggaagcggca   780
gctgagaagg aggttcaagg gaaagcccgg ctccaggact ttattgagaa tctgttacag   840
cgggtagaac tggcggagaa gcagcttgag tactatcaga gccagcaggc ctctggcttt   900
gtccgtgatc tcagcgggca cgtgagctgg aaaggtgctg gcgaagctcg cctggtgtgc   960
caaaatgacc tggaattgga ggagtctgcg attgtggaat aa                      1002
```

<210> SEQ ID NO 4
<211> LENGTH: 333
<212> TYPE: PRT
<213> ORGANISM: Homo sapiens

<400> SEQUENCE: 4

Met Gln Gln Lys Ala Phe Glu Glu Ser Arg Tyr Pro Trp Gln Glu Ser
1               5                   10                  15

Phe Glu Asn Val Ala Val Cys Leu Pro Leu Arg Cys Pro Arg Cys Gly
                20                  25                  30

Asp His Thr Arg Phe Arg Ser Leu Ser Ser Leu Arg Ala His Leu Glu
            35                  40                  45

Phe Ser His Ser Tyr Glu Glu Arg Thr Leu Leu Thr Lys Cys Ser Leu
        50                  55                  60

Phe Pro Ser Leu Lys Asp Thr Asp Leu Val Thr Ser Ser Glu Leu Leu
65                  70                  75                  80

Lys Pro Gly Lys Leu Gln Ser Ser Gly Asn Val Val Lys Gln Lys Pro

|   |   |   |   | 85 |   |   |   | 90 |   |   |   | 95 |   |   |
|---|---|---|---|---|---|---|---|---|---|---|---|---|---|---|
Ser | Tyr | Val | Asn | Leu | Tyr | Ser | Ile | Ser | His | Glu | His | Ser | Lys | Asp | Arg

```
            Ser Tyr Val Asn Leu Tyr Ser Ile Ser His Glu His Ser Lys Asp Arg
                             85                  90                  95

Lys Pro Phe Glu Val Val Ala Glu Arg Pro Val Ser Tyr Val Gln Thr
                        100                 115                 125
                                 Lys Pro Phe Glu Val Val Ala Glu Arg Pro Val Ser Tyr Val Gln Thr
```

Ser Tyr Val Asn Leu Tyr Ser Ile Ser His Glu His Ser Lys Asp Arg
                                100                 105                 110

Lys Pro Phe Glu Val Val Ala Glu Arg Pro Val Ser Tyr Val Gln Thr
            115                 120                 125

Tyr Thr Ala Met Asp Leu His Ala Asp Ser Leu Asp Gly Thr Arg Ser
            130                 135                 140

Gly Pro Gly Leu Pro Thr Ser Asp Thr Lys Ala Ser Phe Glu Ala His
145                 150                 155                 160

Val Arg Glu Lys Phe Asn Arg Met Val Glu Ala Val Asp Arg Thr Ile
                        165                 170                 175

Glu Lys Arg Ile Asp Lys Leu Thr Lys Glu Leu Ala Gln Lys Thr Ala
                180                 185                 190

Glu Leu Leu Glu Val Arg Ala Ala Phe Val Gln Leu Thr Gln Lys Lys
            195                 200                 205

Gln Glu Val Gln Arg Arg Glu Arg Ala Leu Asn Arg Gln Val Asp Val
            210                 215                 220

Ala Val Glu Met Ile Ala Val Leu Arg Gln Arg Leu Thr Glu Ser Glu
225                 230                 235                 240

Glu Glu Leu Leu Arg Lys Glu Glu Val Val Thr Phe Asn His Phe
                    245                 250                 255

Leu Glu Ala Ala Ala Glu Lys Glu Val Gln Gly Lys Ala Arg Leu Gln
            260                 265                 270

Asp Phe Ile Glu Asn Leu Leu Gln Arg Val Glu Leu Ala Glu Lys Gln
                275                 280                 285

Leu Glu Tyr Tyr Gln Ser Gln Gln Ala Ser Gly Phe Val Arg Asp Leu
        290                 295                 300

Ser Gly His Val Ser Trp Lys Gly Ala Gly Glu Ala Arg Leu Val Cys
305                 310                 315                 320

Gln Asn Asp Leu Glu Leu Glu Glu Ser Ala Ile Val Glu
                    325                 330

<210> SEQ ID NO 5
<211> LENGTH: 1389
<212> TYPE: DNA
<213> ORGANISM: Homo sapiens

<400> SEQUENCE: 5
atgcaacaga aggcttttga ggaaagcaga tatccctggc aggagtcctt tgagaatgtt      60
gctgtgtgcc tgccattacg ctgcccgagg tgtggagacc ataccagatt tagaagcttg     120
tcatccttga gggcccatct ggagttcagt cacagctacg aagaaagaac cctcttgaca     180
aaatgcagtc tctttccatc cctcaaagac acagacctag tcacttcctc agaactcctg     240
aaaccgggaa aattgcagag cagtggcaac gtggtaaagc agaaaccgag ctatgttaac     300
ttgtacagca tttcacatga acattccaag gacaggaagc catttgaggt ggtggcagag     360
aggcctgtgt cctatgtgca gacctacact gccatggacc tccatgcaga ctcgctggat     420
gggacacggt cgggtcctgg actgcccacc tcagacacca agcttctttt cgaggcacat     480
gtcagagaaa aattcaatcg aatggttgag gctgtggata ggaccattga aagagaatt      540
gataaactca ccaaagagtt ggcccagaaa actgcggaac tgttggaagt cgggcagct      600
tttgtgcagc tgactcagaa aaagcaggaa gttcagagac gagagcgggc cttaaacaga     660
caggtggacg tggccgtgga aatgatagct gtactgaggc aacgcctgac ggaatctgag     720
```

```
gaggagcttc ttaggaaaga agaagaagtt gtcacattca accatttcct ggaagcggca      780
gctgagaagg aggttcaagg gaaagcccgg ctccaggact ttattgagaa tctgttacag      840
cgggtagaac tggcggagaa gcagcttgag tactatcaga gccagcaggc ctctggcttt      900
gtccgtgatc tcagcgggca cgtgagctgg aaaggtgctg cgaagctcg  cctggtgtgc      960 caaaatgacc tggaattgga gattttggc  catataaacc accatctttc ggggttgaaa     1020
gattctcatt gtctagtttt tctgcaagcc ccacctgtgc cctggatcat tttagccagc     1080
tttctctgga ttctcggaaa tccctggacg tcttccacgg ctactgcagg atttagccaa     1140
atttgggtgc tatttccctt tgtggaggg  acttttcatc acaatgagaa ggacgtctta     1200
ggactccagg actttgagag agaaagtgtc tctacaagtc aaagcaggaa tatcagcctt     1260
cttacactag gacaactcca aaattgtgtg attggcaaat tgacaatcat cgatttgttg     1320
actgaacacc tgttaggtgt aaggcacggt gtcatatgct tccttgggg  cttgccttca     1380 agcagctaa                                                              1389
```

<210> SEQ ID NO 6
<211> LENGTH: 462
<212> TYPE: PRT
<213> ORGANISM: Homo sapiens

<400> SEQUENCE: 6

```
Met Gln Gln Lys Ala Phe Glu Glu Ser Arg Tyr Pro Trp Gln Glu Ser
1               5                   10                  15

Phe Glu Asn Val Ala Val Cys Leu Pro Leu Arg Cys Pro Arg Cys Gly
                20                  25                  30

Asp His Thr Arg Phe Arg Ser Leu Ser Ser Leu Arg Ala His Leu Glu
            35                  40                  45

Phe Ser His Ser Tyr Glu Glu Arg Thr Leu Leu Thr Lys Cys Ser Leu
    50                  55                  60

Phe Pro Ser Leu Lys Asp Thr Asp Leu Val Thr Ser Ser Glu Leu Leu
65                  70                  75                  80

Lys Pro Gly Lys Leu Gln Ser Ser Gly Asn Val Val Lys Gln Lys Pro
                85                  90                  95

Ser Tyr Val Asn Leu Tyr Ser Ile Ser His Glu His Ser Lys Asp Arg
                100                 105                 110

Lys Pro Phe Glu Val Val Ala Glu Arg Pro Val Ser Tyr Val Gln Thr
            115                 120                 125

Tyr Thr Ala Met Asp Leu His Ala Asp Ser Leu Asp Gly Thr Arg Ser
    130                 135                 140

Gly Pro Gly Leu Pro Thr Ser Asp Thr Lys Ala Ser Phe Glu Ala His
145                 150                 155                 160

Val Arg Glu Lys Phe Asn Arg Met Val Glu Ala Val Asp Arg Thr Ile
                165                 170                 175

Glu Lys Arg Ile Asp Lys Leu Thr Lys Glu Leu Ala Gln Lys Thr Ala
            180                 185                 190

Glu Leu Leu Glu Val Arg Ala Ala Phe Val Gln Leu Thr Gln Lys Lys
    195                 200                 205

Gln Glu Val Gln Arg Arg Glu Arg Ala Leu Asn Arg Gln Val Asp Val
    210                 215                 220

Ala Val Glu Met Ile Ala Val Leu Arg Gln Arg Leu Thr Glu Ser Glu
225                 230                 235                 240

Glu Glu Leu Leu Arg Lys Glu Glu Val Val Thr Phe Asn His Phe
                245                 250                 255
```

Leu Glu Ala Ala Ala Glu Lys Glu Val Gln Gly Lys Ala Arg Leu Gln
            260                 265                 270

Asp Phe Ile Glu Asn Leu Leu Gln Arg Val Glu Leu Ala Glu Lys Gln
        275                 280                 285

Leu Glu Tyr Tyr Gln Ser Gln Gln Ala Ser Gly Phe Val Arg Asp Leu
    290                 295                 300

Ser Gly His Val Ser Trp Lys Gly Ala Gly Glu Ala Arg Leu Val Cys
305                 310                 315                 320

Gln Asn Asp Leu Glu Leu Glu Ile Phe Gly His Ile Asn His His Leu
                325                 330                 335

Ser Gly Leu Lys Asp Ser His Cys Leu Val Phe Leu Gln Ala Pro Pro
            340                 345                 350

Val Pro Trp Ile Ile Leu Ala Ser Phe Leu Trp Ile Leu Gly Asn Pro
        355                 360                 365

Trp Thr Ser Ser Thr Ala Thr Ala Gly Phe Ser Gln Ile Trp Val Leu
    370                 375                 380

Phe Pro Phe Cys Gly Gly Thr Phe His His Asn Glu Lys Asp Val Leu
385                 390                 395                 400

Gly Leu Gln Asp Phe Glu Arg Glu Ser Val Ser Thr Ser Gln Ser Arg
                405                 410                 415

Asn Ile Ser Leu Leu Thr Leu Gly Gln Leu Gln Asn Cys Val Ile Gly
            420                 425                 430

Lys Leu Thr Ile Ile Asp Leu Leu Thr Glu His Leu Leu Gly Val Arg
        435                 440                 445

His Gly Val Ile Cys Phe Pro Trp Gly Leu Pro Ser Ser Ser
    450                 455                 460

<210> SEQ ID NO 7
<211> LENGTH: 651
<212> TYPE: DNA
<213> ORGANISM: Homo sapiens

<400> SEQUENCE: 7
atgtctgcgc tgggtcagat aaccatcact gtctccaggt gctggaatac agagaggaac    60
caaacagata aaatccttg cctgcacgga gcttaccttc agctaaggga gacagtcaaa    120
aacaagtcaa cacatctaaa gaagccactg atgaaacagg ctccccttg aaagaccat    180 ctcgccttcc aacctctcca tcctgcagag aggaaaaccc aagtttggcg ttggcagtca    240
ggtaattcat cagatctgga aaccacctca tcagcatccc cctggccaac tggaagcaac    300
cgtgacgttg tgctgaatac acttgcagag tcgtgctgtg gtctctccga gctcatcacg    360
gcacctccct atgcaggagt ttcaattcaa ggatttagcc aaatttgggt gctatttccc    420
ttttgtggag ggacttttca tcacaatgag aaggacgtct taggactcca ggactttgag    480
agagaaagtg tctctacaag tcaaagcagg aatatcagcc ttcttacact aggacaactc    540
caaaattgtg tgattggcaa attgacaatc atcgatttgt tgactgaaca cctgttaggt    600
gtaaggcacg gtgtcatatg ctttccttgg ggcttgcctt caagcagcta a    651

<210> SEQ ID NO 8
<211> LENGTH: 216
<212> TYPE: PRT
<213> ORGANISM: Homo sapiens

<400> SEQUENCE: 8

Met Ser Ala Leu Gly Gln Ile Thr Ile Thr Val Ser Arg Cys Trp Asn

```
1               5                   10                  15
Thr Glu Arg Asn Gln Thr Asp Lys Asn Pro Cys Leu His Gly Ala Tyr
                20                  25                  30
Leu Gln Leu Arg Glu Thr Val Lys Asn Lys Ser Thr His Leu Lys Lys
            35                  40                  45
Pro Leu Met Lys Gln Ala Pro Pro Trp Lys Asp His Leu Ala Phe Gln
        50                  55                  60
Pro Leu His Pro Ala Glu Arg Lys Thr Gln Val Trp Arg Trp Gln Ser
65                  70                  75                  80
Gly Asn Ser Ser Asp Leu Glu Thr Thr Ser Ser Ala Ser Pro Trp Pro
                85                  90                  95
Thr Gly Ser Asn Arg Asp Val Val Leu Asn Thr Leu Ala Glu Ser Cys
            100                 105                 110
Cys Gly Leu Ser Glu Leu Ile Thr Ala Pro Pro Tyr Ala Gly Val Ser
        115                 120                 125
Ile Gln Gly Phe Ser Gln Ile Trp Val Leu Phe Pro Phe Cys Gly Gly
        130                 135                 140
Thr Phe His His Asn Glu Lys Asp Val Leu Gly Leu Gln Asp Phe Glu
145                 150                 155                 160
Arg Glu Ser Val Ser Thr Ser Gln Ser Arg Asn Ile Ser Leu Leu Thr
                165                 170                 175
Leu Gly Gln Leu Gln Asn Cys Val Ile Gly Lys Leu Thr Ile Ile Asp
                180                 185                 190
Leu Leu Thr Glu His Leu Leu Gly Val Arg His Gly Val Ile Cys Phe
            195                 200                 205
Pro Trp Gly Leu Pro Ser Ser Ser
        210                 215

<210> SEQ ID NO 9
<211> LENGTH: 1227
<212> TYPE: DNA
<213> ORGANISM: Mus sp.

<400> SEQUENCE: 9
atgcaacaga cgacttttga ggaaagccgg taccattggc aggactcgct ggagaatgtc    60
gctgtgtgcc tgccattccg ctgcccgagg tgtggagacc ataccagatt tagaagcttg   120
tcatccttga gggcccatct ggaattcagt cacagctacg aagagcggac cctcctgaca   180
aaatgcagcc tcctgccctc tctcaaggac acagagcttc tcaggtcctc ggaactcccg   240
aagcagggaa aagtactccg gggccacgca aggtgaccca gcagaagtc gagctatgtt   300
aacttgtaca gcatctccca cgggcactcc aaggacacga acccttttga tggtggca    360
gagaggcccg tgtcctatgt gcagacctac acggccgtgg acatccgggc tgactctctg   420
gatgctccct gcgccagccc tggtctcccc acccaagata ccaaagctgc tttcgaggct   480
cacgtccgag aaaagttcaa tcgcatggta gaggccgtgg acaggaccat cgagaagaga   540
atcgacaaac tcaccaaaga gttggcccag aaaaccgccg aactgttgga agtccgggca   600
gcctttgcgc agctgactca agaagcag gaggtccaga ggagagagcg ggccctgaac   660
aaacaggtag atgtggccgt ggaaatgatc gcagtgctga gcagcgtct gacggaatcc   720
gaggaggagc tcctgaggaa agaggaagaa gtcgtcacat tcaaccattt cctggaggca   780
gcggctgaga aggaggttca ggaaaaagcg aggctccagg actttattga aaatctgctg   840
caacgggtag aattggcgga gaagcagttg gaatattatc aaagccagca agcctccggt   900
```

```
tttagctgtg acactagtga gcatatgctc acagacatcc catcgaacag gaagcccaga    960
tgcctaagcc gagggcacca gcattctgtt tgcaaccatc ctgagatgag ggcccatttc   1020
catctgaagg ggagaagcta cctgaagaaa gccaaggatg agcgagccgg gatgcagccc   1080
gccaaggcca ttcacgaacc ggctgagtct ccaagagaat tcttcagacc agccaagaaa   1140
ggggaacacc tgggtctgag ccggaaaggg aatttcaggc ccaaaatggc taaaagaag    1200
cctacagcaa tcgtgaatat catctag                                       1227
```

<210> SEQ ID NO 10
<211> LENGTH: 408
<212> TYPE: PRT
<213> ORGANISM: Mus sp.

<400> SEQUENCE: 10

```
Met Gln Gln Thr Thr Phe Glu Glu Ser Arg Tyr His Trp Gln Asp Ser
1               5                   10                  15

Leu Glu Asn Val Ala Val Cys Leu Pro Phe Arg Cys Pro Arg Cys Gly
            20                  25                  30

Asp His Thr Arg Phe Arg Ser Leu Ser Ser Leu Arg Ala His Leu Glu
        35                  40                  45

Phe Ser His Ser Tyr Glu Glu Arg Thr Leu Leu Thr Lys Cys Ser Leu
    50                  55                  60

Leu Pro Ser Leu Lys Asp Thr Glu Leu Leu Arg Ser Ser Glu Leu Pro
65                  70                  75                  80

Lys Gln Gly Lys Val Leu Arg Gly His Ala Lys Val Thr Lys Gln Lys
                85                  90                  95

Ser Ser Tyr Val Asn Leu Tyr Ser Ile Ser His Gly His Ser Lys Asp
            100                 105                 110

Thr Lys Pro Phe Glu Met Val Ala Glu Arg Pro Val Ser Tyr Val Gln
        115                 120                 125

Thr Tyr Thr Ala Val Asp Ile Arg Ala Asp Ser Leu Asp Ala Pro Cys
    130                 135                 140

Ala Ser Pro Gly Leu Pro Thr Gln Asp Thr Lys Ala Ala Phe Glu Ala
145                 150                 155                 160

His Val Arg Glu Lys Phe Asn Arg Met Val Glu Ala Val Asp Arg Thr
                165                 170                 175

Ile Glu Lys Arg Ile Asp Lys Leu Thr Lys Glu Leu Ala Gln Lys Thr
            180                 185                 190

Ala Glu Leu Leu Glu Val Arg Ala Ala Phe Ala Gln Leu Thr Gln Lys
        195                 200                 205

Lys Gln Glu Val Gln Arg Arg Glu Arg Ala Leu Asn Lys Gln Val Asp
    210                 215                 220

Val Ala Val Glu Met Ile Ala Val Leu Lys Gln Arg Leu Thr Glu Ser
225                 230                 235                 240

Glu Glu Glu Leu Leu Arg Lys Glu Glu Glu Val Val Thr Phe Asn His
                245                 250                 255

Phe Leu Glu Ala Ala Ala Glu Lys Glu Val Gln Gly Lys Ala Arg Leu
            260                 265                 270

Gln Asp Phe Ile Glu Asn Leu Leu Gln Arg Val Glu Leu Ala Glu Lys
        275                 280                 285

Gln Leu Glu Tyr Tyr Gln Ser Gln Gln Ala Ser Gly Phe Ser Cys Asp
    290                 295                 300

Thr Ser Glu His Met Leu Thr Asp Ile Pro Ser Asn Arg Lys Pro Arg
305                 310                 315                 320
```

```
Cys Leu Ser Arg Gly His Gln His Ser Val Cys Asn His Pro Glu Met
                325                 330                 335

Arg Ala His Phe His Leu Lys Gly Arg Ser Tyr Leu Lys Ala Lys
            340                 345                 350

Asp Glu Arg Ala Gly Met Gln Pro Ala Lys Ala Ile His Glu Pro Ala
            355                 360                 365

Glu Ser Pro Arg Glu Phe Phe Arg Pro Ala Lys Lys Gly Glu His Leu
        370                 375                 380

Gly Leu Ser Arg Lys Gly Asn Phe Arg Pro Lys Met Ala Lys Lys Lys
385                 390                 395                 400

Pro Thr Ala Ile Val Asn Ile Ile
                405

<210> SEQ ID NO 11
<211> LENGTH: 407
<212> TYPE: PRT
<213> ORGANISM: Homo sapiens

<400> SEQUENCE: 11

Met Gln Gln Lys Ala Phe Glu Glu Ser Arg Tyr Pro Trp Gln Glu Ser
1               5                   10                  15

Phe Glu Asn Val Ala Val Cys Leu Pro Leu Arg Cys Pro Arg Cys Gly
                20                  25                  30

Asp His Thr Arg Phe Arg Ser Leu Ser Ser Leu Arg Ala His Leu Glu
            35                  40                  45

Phe Ser His Ser Tyr Glu Glu Arg Thr Leu Leu Thr Lys Cys Ser Leu
50                  55                  60

Phe Pro Ser Leu Lys Asp Thr Asp Leu Val Thr Ser Ser Glu Leu Leu
65                  70                  75                  80

Lys Pro Gly Lys Leu Gln Ser Ser Gly Asn Val Val Lys Gln Lys Pro
                85                  90                  95

Ser Tyr Val Asn Leu Tyr Ser Ile Ser His Glu His Ser Lys Asp Arg
                100                 105                 110

Lys Pro Phe Glu Val Val Ala Glu Arg Pro Val Ser Tyr Val Gln Thr
            115                 120                 125

Tyr Thr Ala Met Asp Leu His Ala Asp Ser Leu Asp Gly Thr Arg Ser
130                 135                 140

Gly Pro Gly Leu Pro Thr Ser Asp Thr Lys Ala Ser Phe Glu Ala His
145                 150                 155                 160

Val Arg Glu Lys Phe Asn Arg Met Val Glu Ala Val Asp Arg Thr Ile
                165                 170                 175

Glu Lys Arg Ile Asp Lys Leu Thr Lys Glu Leu Ala Gln Lys Thr Ala
            180                 185                 190

Glu Leu Leu Glu Val Arg Ala Ala Phe Val Gln Leu Thr Gln Lys Lys
        195                 200                 205

Gln Glu Val Gln Arg Arg Glu Arg Ala Leu Asn Arg Gln Val Asp Val
    210                 215                 220

Ala Val Glu Met Ile Ala Val Leu Arg Gln Arg Leu Thr Glu Ser Glu
225                 230                 235                 240

Glu Glu Leu Leu Arg Lys Glu Glu Val Val Thr Phe Asn His Phe
                245                 250                 255

Leu Glu Ala Ala Ala Glu Lys Gly Val Gln Gly Lys Ala Arg Leu Gln
            260                 265                 270

Asp Phe Ile Glu Asn Leu Leu Gln Arg Val Glu Leu Ala Glu Lys Gln
```

```
           275                 280                 285
Leu Glu Tyr Tyr Gln Ser Gln Gln Ala Ser Gly Phe Val Arg Asp Leu
        290                 295                 300

Ser Gly His Val Leu Thr Asp Ile Ser Ser Asn Arg Lys Pro Lys Cys
305                 310                 315                 320

Leu Ser Arg Gly His Pro His Ser Val Cys Asn His Pro Asp Leu Lys
                325                 330                 335

Ser His Phe His Pro Lys Gly Arg Asn His Leu Lys Lys Ala Lys Asp
                340                 345                 350

Asp Arg Ala Ser Met Gln Pro Ala Lys Ala Ile His Glu Gln Ala Glu
        355                 360                 365

Ser Ser Arg Asp Leu Cys Arg Pro Pro Lys Lys Gly Glu Leu Leu Gly
        370                 375                 380

Phe Gly Arg Lys Gly Asn Ile Arg Pro Lys Met Ala Lys Lys Lys Pro
385                 390                 395                 400

Thr Ala Ile Val Asn Ile Ile
                405
```

US 10,378,060 B2

ZNF365/ZFP365 BIOMARKER PREDICTIVE OF ANTI-CANCER RESPONSE

CROSS-REFERENCE TO RELATED APPLICATIONS

This application claims the benefit of U.S. Provisional Application No. 61/547,212, filed on Oct. 14, 2011; the entire content of said applications is incorporated herein in its entirety by this reference.

GOVERNMENT FUNDING

This invention was made with government support under grant number R01 CA084628 awarded by The National Institutes of Health. The government has certain rights in the invention.

BACKGROUND OF THE INVENTION

Medical oncologists have benefited greatly from relatively recent efforts to dissect and understand the genetic elements underlying mammalian cancer. The identification of specific genetic predispositions, such as mutations in BRCA-1, BRCA2, PARP-1, PARP-2, and DNA-PK, has provided key insights into the mechanisms underlying tumorigenesis and has proven useful for the design of new generations of targeted approaches for clinical intervention. For example, extreme responsiveness of tumors defective in homologous recombination because of BRCA mutations to inhibitors of PARP, a mediator of DNA repair, has recently been elucidated. With the determination of the human genome sequence and improvements in sequencing and bioinformatics technologies, systematic analyses of genetic alterations in human cancers have become possible. Clinical interventions based upon this information have, however, been severely hampered by the fact that often only a percentage of patients will respond favorably to a particular anti-cancer treatment. Medical oncologists currently cannot accurately predict which patients will or will not respond to a given anti-cancer regimen. Accordingly, there is a great need in the art to identify biomarkers which are predictive of patient responsiveness to anti-cancer therapies.

SUMMARY OF THE INVENTION

The present invention is based, at least in part, on the discovery that the amount (e.g., copy number or level of expression) and/or activity of ZNF365/ZFP365 is predictive of anti-cancer response of hyperproliferative cells to anti-cancer therapies.

In one aspect, a method of identifying the likelihood of a cancer in a subject to be responsive to an anti-cancer therapy comprises measuring the copy number of ZNF365 in a sample is provided, wherein the sample comprises nucleic acid molecules (e.g., at least one cell) from the subject, and comparing said copy number to that of a control sample, wherein an increased copy number of ZNF365 in the sample relative to the control sample identifies the cancer as being more likely to be responsive to the anti-cancer therapy and wherein a decreased copy number of ZNF365 in the sample relative to the control sample identifies the cancer as being less likely to be responsive to the anti-cancer therapy. In one embodiment, ZNF365 or ZFP365 reduces DNA repair activity (e.g., non-homologous end joining, homologous recombination, and/or DNA single-strand break repair). In another embodiment, ZNF365 or ZFP365 interacts with PARP-1, PARP-2, DNA-PK, Ku70, MRE11, RPA, CHEK1, and/or topoisomerases. In still another embodiment, ZNF365 or ZFP365 is selected from the group consisting of SEQ ID NOs:1-10 or a fragment thereof. In yet another embodiment, the copy number is assessed by fluorescent in situ hybridization (FISH), quantitative PCR (qPCR), comparative genomic hybridization (CGH), or single-molecule sequencing. In another embodiment, the control sample contains cells having a normal copy number of ZNF 365 in the species to which the subject belongs. In still another embodiment, the cancer is selected from the group consisting of brain cancer, breast cancer, ovarian cancer, and pancreatic cancer. In yet another embodiment, cells are cancer cells harboring defects in genes encoding proteins mediating non-homologous end joining, homologous recombination, or DNA single-strand break repair (e.g., cells harboring defects in BRCA1, BRCA2, and/or Fanconi anemia (FANC) genes). In another embodiment, the subject is a human. In still another embodiment, the anti-cancer treatment is selected from the group consisting of chemotherapy (e.g., inhibitors selected from the group consisting of inhibitors of PARP-1, PARP-2, DNA-PK, Ku70, MRE11, RPA, CHEK1, and topoisomerases), radiation therapy, gene therapy, or a combination thereof. In yet another embodiment, the subject and/or control sample is selected from the group consisting of cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow. In another embodiment, the subject and/or control sample is obtained before or after the subject has received adjuvant chemotherapy. In still another embodiment, the control sample is determined from a non-cell hyperproliferative cell sample from the patient or member of the same species to which the patient belongs. In yet another embodiment, the control sample is a pre-determined amount or activity of ZNF365 or ZFP365 or the average amount or activity of ZNF365 or ZFP365 within the same ethnic group within the species to which the subject belongs. In another embodiment, the control sample comprises non-cancerous cells from the same tissue type or a different tissue type as that from which said subject sample originated. In still another embodiment, the control sample is from cancerous cells known to be sensitive or insensitive to the anti-cancer therapy (e.g., chemotherapy, such as inhibitors of PARP-1, PARP-2, DNA-PK, Ku70, MRE11, RPA, CHEK1, and topoisomerases; or radiation therapy; or a combination of chemotherapy and radiation therapy). In yet another embodiment, the response to the anti-cancer therapy is measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In another embodiment, the method further comprises treating cancer in the subject, wherein a therapeutically effective amount of the anti-cancer therapy is administered if the patient is determined to be responsive to the anti-cancer therapy (e.g., chemotherapy, such as the use of inhibitors of PARP-1, PARP-2, DNA-PK, Ku70, MRE11, RPA, CHEK1, and topoisomerases; or radiation therapy; or a combination of chemotherapy and radiation therapy.)

In another aspect, a method of identifying the likelihood of a cancer in a subject to be responsive to an anti-cancer therapy is provided, wherein the method comprises a) measuring the amount or activity of ZNF365 or ZFP365 in a subject sample and b) comparing said amount or activity of ZNF365 or ZFP365 to that of a control sample, wherein a significantly increased amount or activity of ZNF365 in the subject sample relative to the control sample identifies the cancer as being more likely to be responsive to the anti-cancer therapy and wherein a decreased amount or activity of ZNF365 in the subject sample relative to the control sample identifies the cancer as being less likely to be responsive to the anti-cancer therapy. In one embodiment, the cancer is selected from the group consisting of brain cancer, breast cancer, ovarian cancer, and pancreatic cancer. In another embodiment, cancer cells harbor defects in genes encoding proteins mediating non-homologous end joining, homologous recombination, or DNA single-strand break repair (e.g., defects in BRCA1, BRCA2, and/or Fanconi anemia (FANC) genes). In still another embodiment, the subject is a human. In yet another embodiment, the anti-cancer treatment is selected from the group consisting of chemotherapy, such as the use of inhibitors of PARP-1, PARD-2, DNA-PK, Ku70, MRE11, RPA, CHEK1, and topoisomerases; or radiation therapy; or a combination of chemotherapy and radiation therapy. In another embodiment, ZNF365 or ZFP365 is selected from the group consisting of SEQ ID NOs:1-10 or a fragment thereof. In still another embodiment, ZNF365 or ZFP365 reduces DNA repair activity. In yet another embodiment, the DNA repair activity is selected from the group consisting of non-homologous end joining, homologous recombination, and DNA single-strand break repair. In another embodiment, ZNF365 or ZFP365 interacts with PARP-1, PARP-2, DNA-PK, Ku70, MRE11, RPA, CHEK1, or topoisomerases. In still another embodiment, the amount of ZNF365 or ZFP365 is determined by determining the level of expression of ZNF365 or ZFP365, determining germline copy number of ZNF365, or determining somatic copy number of ZNF365. In yet another embodiment, the level of expression of ZNF365 or ZFP365 in the subject and/or control samples is assessed by detecting the presence in the subject and/or control sample of a protein corresponding to ZNF365/ZFP365 (e.g., using a reagent which specifically binds with the protein, optionally wherein the reagent is selected from the group consisting of an antibody, an antibody derivative, and an antibody fragment). In another embodiment, the level of expression of ZNF365 or ZFP365 in the subject and/or control sample is assessed by detecting the presence in the subject and/or control sample of a transcribed ZNF365 polynucleotide or portion thereof (e.g., an mRNA or cDNA). In still another embodiment, the step of detecting further comprises amplifying the transcribed polynucleotide. In yet another embodiment, the level of expression of ZNF365 or ZFP365 in the subject and/or control sample is assessed by detecting the presence in the subject and/or control sample of a transcribed ZNF365 polynucleotide which anneals with ZNF365 or anneals with a portion of a ZNF365 polynucleotide, under stringent hybridization conditions. In another embodiment, the subject and/or control sample is selected from the group consisting of cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow. In still another embodiment, the subject and/or control sample is obtained before or after the subject has received adjuvant chemotherapy. In yet another embodiment, the control sample is determined from a non-cell hyperproliferative cell sample from the patient or member of the same species to which the patient belongs. In another embodiment, the control sample is a pre-determined amount or activity of ZNF365 or ZFP365 or the average amount or activity of ZNF365 or ZFP365 within the same ethnic group within the species to which the subject belongs. In still another embodiment, the control sample comprises non-cancerous cells from the same or a different tissue type as that from which said subject sample originated. In yet another embodiment, the control sample is from cancerous cells known to be sensitive or insensitive to the anti-cancer therapy. In another embodiment, the anti-cancer therapy is chemotherapy, such as the use of inhibitors of PARP-1, PARD-2, DNA-PK, Ku70, MRE11, RPA, CHEK1, and topoisomerases, or radiation therapy or a combination of chemotherapy and radiation therapy). In still another embodiment, the response to the anti-cancer therapy is measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In yet another embodiment, the method further comprises treating cancer in the subject, wherein a therapeutically effective amount of the anti-cancer therapy is administered if the patient is determined to be responsive to the anti-cancer therapy (e.g., chemotherapy, such as the use of inhibitors of PARP-1, PARP-2, DNA-PK, Ku70, MRE11, RPA, CHEK1, and topoisomerases) or radiation therapy or a combination of chemotherapy and radiation therapy).

BRIEF DESCRIPTION OF THE DRAWINGS

Figure 3:
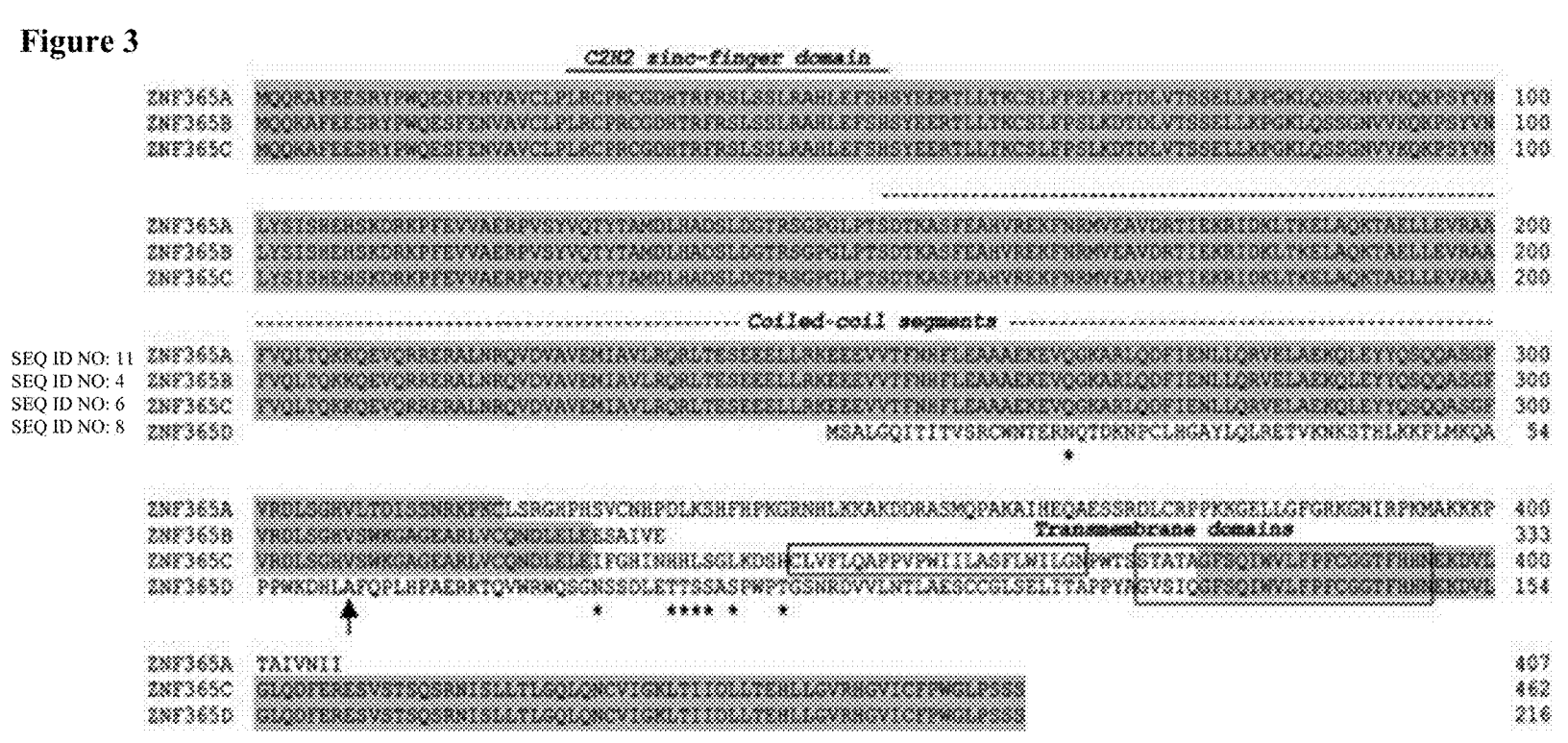

FIG. 3 shows the sequences of human ZNF365 protein isoforms as described in Gianfrancesco et al. (2003) *Am. J. Hum. Genet.* 72:1479-1491.

FIG. 4 shows a list of genes induced upon p53 activation in cells having telomere-dysfunction and genomic instability ranked in order of descending p-values.

FIG. 10A shows staining for DSB as measured by 53BP1-positive DNA damage foci. FIG. 10B shows quantitation of the 53BP1-positive DNA damage foci shown in the upper panels of FIG. 10A. FIG. 10C shows a quantitation of the 53BP1-positive DNA damage foci observed in the lower panels of FIG. 10B in which ZNF365-deficient cells were also treated with 1 μM of the PARP inhibitor, ABT888.

BRIEF DESCRIPTION OF THE TABLES

Figure 1:
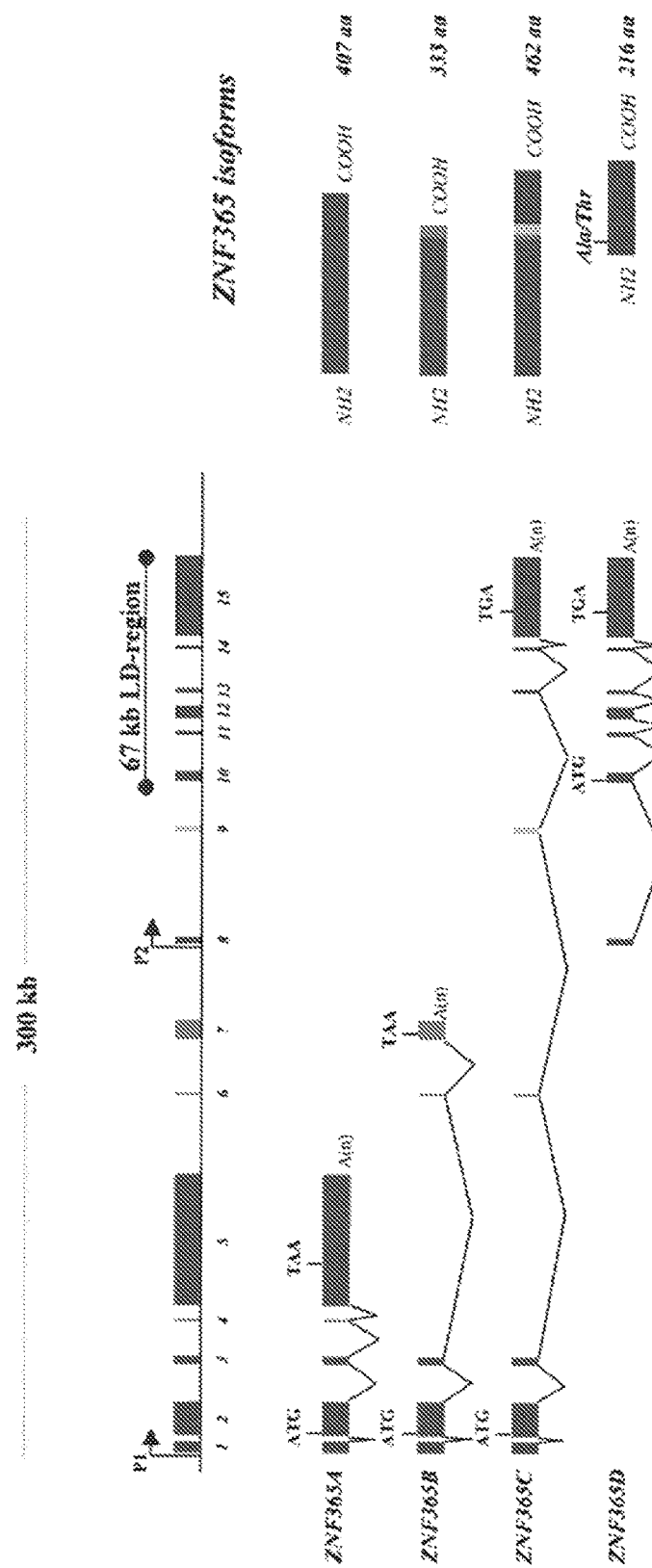
FIG. 1 shows a schematic diagram of human ZNF365 splice variants and protein isoforms as described in Gianfrancesco et al. (2003) *Am. J. Hum. Genet.* 72:1479-1491.

Table 1 shows a list of representative ZNF365/ZFP365 nucleic acid and amino acid sequences from various organisms.

Table 2 shows a list of representative human and mouse nucleic acid and amino acid sequences for markers analyzed in the Examples and useful for the present invention described herein.

DETAILED DESCRIPTION OF THE INVENTION

In the course of biochemical and functional analyses of p53 responsive targets that are altered in response to telomere dysfunction, ZNF365/ZFP365 was identified and described herein as a suppressor of DNA repair mechanisms (e.g., non-homologous end joining (NHEJ), homologous recombination (HR), and DNA single-strand break repair). Enforced ZNF365/ZFP365 overexpression was determined herein to lead to high basal levels of DNA damage checkpoint response, G2/M arrest, and senescence/cell death, whereas siRNA-mediated knockdown of ZNF365/ZFP365 had the opposite effect. ZNF365/ZFP365 has also been shown herein to physically interact with mediators of DNA repair pathways in mammals, including PARP-1/PARP-2. Specifically, further studies demonstrated that increased ZNF365/ZFP365 expression levels in hyperproliferative cells led to decreased responses of those cells to treatment with anti-cancer agents, such as inhibitors of the DNA repair proteins, PARP1/2 and DNA-PK. Accordingly, the present invention relates to methods for predicting response of a cancer in a subject to anti-cancer therapies based upon a determination and analysis of ZNF365/ZFP365 amount (e.g., copy number or level of expression) and/or activity relative to a control. In addition, such analyses can be used in order to provide useful anti-cancer treatment regimens (e.g., based on predictions of subject survival or relapse, timing of adjuvant or neoadjuvant treatment, etc.).

I. Definitions

The articles "a" and "an" are used herein to refer to one or to more than one (i.e. to at least one) of the grammatical object of the article. By way of example, "an element" means one element or more than one element.

The term "altered amount" of ZNF365/ZFP365 or "altered level" of ZNF365/ZFP365 refers to increased or decreased copy number (e.g., germline and/or somatic) of ZNF365/ZFP365 or chromosomal region, e.g., increased or decreased expression level in a cancer sample, as compared to the expression level or copy number of ZNF365/ZFP365 in a control sample. The term "altered amount" of ZNF365/ZFP365 also includes an increased or decreased protein level of ZFP365 in a sample, e.g., a cancer sample, as compared to the protein level of ZFP365 in a normal, control sample. Furthermore, an altered amount of ZNF365/ZFP365 may be determined by detecting posttranslational modification such as methylation status of ZFP365, which may affect the expression or activity of ZFP365.

The amount of ZNF365/ZFP365, e.g., expression or copy number of ZNF365/ZFP365, or protein level of ZFP365, in a subject is "significantly" higher or lower than the normal amount of a ZNF365/ZFP365, if the amount of ZNF365/ZFP365 is greater or less, respectively, than the normal level by an amount greater than the standard error of the assay employed to assess amount, and preferably at least twice, and more preferably three, four, five, ten or more times that amount. Alternately, the amount of ZNF365/ZFP365 in the subject can be considered "significantly" higher or lower than the normal amount if the amount is at least about two, and preferably at least about three, four, or five times, higher or lower, respectively, than the normal amount of ZNF365/ZFP365.

The term "altered level of expression" of ZNF365/ZFP365 refers to an expression level or copy number of ZNF365/ZFP365 in a test sample, e.g., a sample derived from a patient suffering from cancer, that is greater or less than the standard error of the assay employed to assess expression or copy number, and is preferably at least twice, and more preferably three, four, five or ten or more times the expression level or copy number of ZNF365/ZFP365 in a control sample (e.g., sample from a healthy subjects not having the associated disease) and preferably, the average expression level or copy number of ZNF365/ZFP365 in several control samples. The altered level of expression is greater or less than the standard error of the assay employed to assess expression or copy number, and is preferably at least twice, and more preferably three, four, five or ten or more times the expression level or copy number of ZNF365/ZFP365 in a control sample (e.g., sample from a healthy subjects not having the associated disease) and preferably, the average expression level or copy number of ZNF365/ZFP365 in several control samples.

The term "altered activity" of ZNF365/ZFP365 refers to an activity of ZNF365/ZFP365 which is increased or decreased in a disease state, e.g., in a cancer sample, as compared to the activity of ZNF365/ZFP365 in a normal, control sample. Altered activity of ZNF365/ZFP365 may be the result of, for example, altered expression of ZNF365/ZFP365, altered protein level of ZNF365/ZFP365, altered structure of ZNF365/ZFP365, or, e.g., an altered interaction with other proteins involved in the same or different pathway as ZNF365/ZFP365 or altered interaction with transcriptional activators or inhibitors.

The term "altered structure" of ZNF365/ZFP365 refers to the presence of mutations or allelic variants within ZNF365/ZFP365 gene or maker protein, e.g., mutations which affect expression or activity of ZNF365/ZFP365, as compared to the normal or wild-type gene or protein. For example, mutations include, but are not limited to substitutions, deletions, or addition mutations. Mutations may be present in the coding or non-coding region of ZNF365.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., ZNF365/ZFP365 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, ZNF365/ZFP365 peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to ZNF365/ZFP365 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to defects in DNA repair (e.g., defects in homologous recombination repair due to, for example, harboring of BRCA1, BRCA2, and/or Fanconi anemia (FANC) gene mutations). For example, it has been demonstrated herein that cells having unregulated or defective ZNF365/ZFP365 expression are hypersensitive to crosslinking agents due to defects in DNA repair. Cancer cells are often in the form of a tumor, but such cells may exist alone within an animal, or may be a non-tumorigenic cancer cell, such as a leukemia cell. As used herein, the term "cancer" includes premalignant as well as malignant cancers. A listing of exemplary, but not limited, cancers is provided in Section IA below.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The "copy number of a gene" or the "copy number of ZNF365/ZFP365" refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of ZNF365 or "normal" level of expression of ZNF365/ZFP365 is the activity/level of expression of ZNF365/ZFP365 or copy number of ZNF365 in a biological sample, e.g., a sample containing tissue, whole blood, serum, plasma, buccal scrape, saliva, cerebrospinal fluid, urine, stool, and bone marrow, from a subject, e.g., a human, not afflicted with cancer.

"DNA repair" as used herein, refers to a collection of mechanisms used to repair damage to DNA. A non-limiting list of exemplary DNA repair mechanisms includes non-homologous end joining (NHEJ), homologous recombination (HR), single-strand break repair, nucleotide excision repair (NER), base excision repair (BER), mismatch excision repair (MER), and other repair mechanisms using DNA polymerases, editing and processing nucleases and DNA repair helicases. Many genes and genetic elements in mammals (e.g., humans) are well known to those of skill in the art and are available in such compiled forms as Wood et al., Human DNA Repair Genes, Science, 291: 1284-1289 (February 2001) and Bulman et al., Locations of DNA Damage Response and Repair Genes in the Mouse and Correlation with Cancer Risk Modifiers, National Radiological Protection Board Report, October 2004 (ISBN 0-85951-544-3). In addition, a mouse DNA repair gene database is publicly available at the UK Health Protection Agency website. Exemplary proteins mediating NHEJ include, but are not limited to, Ligase4, XRCC4, H2AX, DNAPKs (DNA-PK), Ku70, Ku80, Artemis, Cernunnos/XLF, MRE11, NBS1, and RAD50. Exemplary homologous recombination proteins include RAD51, RAD52, RAD54, XRCC3, RAD51C, BRCA1, BRCA2 (FANCD1), FANCA, FANCB, FANCC, FANCD2, FANCE, FANCF, FANCG, FANCJ (BRIP1/BACH1), FANCL, and FANCM. Exemplary proteins mediating BER include, but are not limited to, ung, smug1, mbd4, tdg, off1, myh, nth1, mpg, ape1, ape2, lig3, xrcc1, adprt, adprt12 and adprt13. Exemplary proteins mediating MER include, but are not limited to, msh2, msh3, msh4, msh5, msh6, pms1, pms3, mlh1, mlh3, pms213 and pms214. Exemplary DNA repair helicases include BLM and WRN.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, "homologous recombination" is one type of DNA repair mechanism involving the use of an intact copy of a gene or chromosome as a template for synthesis of new DNA spanning a double strand break. In higher eukaryotes, homologous recombination occurs predominantly in the G2 phase of the cell cycle, when sister chromatids are available as template (Sonoda, E., Takata, M., Yamashita, Y. M., Morrison, C. and Takeda, S. (2001) Homologous DNA recombination in vertebrate cells. Proc. Natl. Acad. Sci. USA, 98, 8388-8394; Lee, S. E., Mitchell, R. A., Cheng, A. and Hendrickson, E. A. (1997) Evidence for DNA-PK-dependent and -independent DNA double-strand break repair pathways in mammalian cells as a function of the cell cycle. Mol. Cell. Biol., 17, 1425-1433). BRCA1 and BRCA2 act as an integral component of the homologous recombination machinery (HR) (Narod S A, Foulkes W D (2004) Nat Rev Cancer 4:665-676; Gudmundsdottir K, Ashworth A (2006) Oncogene 25:5864-5874). Cells defective in BRCA1 or BRCA2 have a defect in the repair of double-strand breaks (DSB) by the mechanism of homologous recombination (HR) by gene conversion (Farmer H, et al. (2005) Nature 434:917-921; Narod S A, Foulkes W D (2004) Nat Rev Cancer 4:665-676; Gudmundsdottir K, Ashworth A (2006) Oncogene 25:5864-5874; Helleday T, et al. (2008) Nat Rev Cancer 8:193-204). Deficiency in either of the breast cancer susceptibility proteins BRCA1 or BRCA2 induces profound cellular sensitivity to the inhibition of poly(ADP-ribose) polymerase (PARP) activity, resulting in cell cycle arrest and apoptosis. It has been reported that the critical role of BRCA1 and BRCA2 in the repair of double-strand breaks by homologous recombination (HR) is the underlying reason for this sensitivity, and the deficiency of RAD51, RAD54, DSS1, RPA1, NBS1, ATR, ATM, CHK1, CHK2, FANCD2, FANCA, or FANCC induces such sensitivity (McCabe N. et. al. Deficiency in the repair of DNA damage by homologous recombination and sensitivity to poly(ADP-ribose) polymerase inhibition, Cancer research 2006, vol. 66, 8109-8115). It has been proposed that PARP1 inhibition can be a specific therapy for cancers with defects in BRCA1/2 or other HR pathway components (Helleday T et al. (2008) Nat Rev Cancer 8:193-204).

As used herein, the term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

As used herein, the term "interaction", when referring to an interaction between two molecules, refers to the physical contact (e.g., binding) of the molecules with one another. Generally, such an interaction results in an activity (which produces a biological effect) of one or both of said molecules.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of ZNF365/ZFP365 polypeptide or fragment thereof, in which the protein is separated from cellular components of the cells from which it is isolated or recombinantly produced. In one embodiment, the language "substantially free of cellular material" includes preparations of ZNF365/ZFP365 protein or fragment thereof, having less than about 30% (by dry weight) of non-ZNF365/ZFP365 protein (also referred to herein as a "contaminating protein"), more preferably less than about 20% of non-ZNF365/ZFP365 protein, still more preferably less than about 10% of non-ZNF365/ZFP365 protein, and most preferably less than about 5% non-ZNF365/ZFP365 protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

As used herein, "non-homologous end-joining" is one type of DNA repair mechanism involving the ligation of DNA termini, typically intermolecular ligation. It includes the joining of DNA ends which exhibit little or no complementarity to each other (and so, typically, each end does not hybridize to the other) and, in any event, is a term well known in the art as is evidenced by its use in many of the papers and patent applications referred to herein, all of which are incorporated herein by reference. Typically, a NHEJ reaction requires a suitable DNA substrate, and suitable components for the reaction of joining the DNA ends to proceed. Suitable DNA substrates are those that, typically, are linear DNA molecules the length of which need only be large enough to accommodate the factors which participate in NHEJ. Conveniently, each DNA fragment to be joined is, independently, at least 50 bp, preferably at least 70 bp, more preferably at least 100 bp but may be bigger. In relation to the observation of a NHEJ reaction, particularly in a screening assay, one or both of the DNA molecules (or DNA ends) to be joined are detectably labeled such as with radiolabelled phosphorus or with fluorescent labels. Although it is convenient to use two separate DNA molecules to be joined in the NHEJ, two ends of the same molecule can be joined such as the ends of a linearized plasmid. NHEJ typically takes place in a eukaryotic cell, such as a vertebrate cell including mammalian cells (although it can also occur in some circumstances in prokaryotes) but, as is described in detail in Baumann & West (1998) Proc. Natl. Acad. Sci. USA 95, 14066-14070, it can also occur in cell-free extracts, such as those obtained from human cells as therein described. Intermolecular ligation in this cell-free system was found to be accurate and to depend on DNA ligase IV, XRCC4 and DNA-dependent protein kinase (DNA-PK; this is a heterotrimer made up of a catalytic subunit DNA-PKcs (encoded by the XRCC7 gene) and two further subunits which are believed to be involved in DNA binding, namely Ku70 and Ku80 subunits (which are encoded by the XRCC6 and XRCC5 genes, respectively). However, it is possible to get a low level of NHEJ with DNA ligase IV and XRCC4 in the absence of DNA-PK, but a greater extent of NHEJ is obtained when DNA ligase IV and XRCC4 are present with Ku70 and Ku80, and still further NHEJ is achieved when the catalytic subunit of DNA-PK is present.

The "normal" level of expression of ZNF365/ZFP365 is the level of expression of ZNF365/ZFP365 in cells of a subject, e.g., a human patient, not afflicted with a cancer, e.g., lung, ovarian, pancreatic, liver, breast, prostate, and colon carcinomas, as well as melanoma and multiple myeloma. An "over-expression" or "significantly higher level of expression" of ZNF365/ZFP365 refers to an expression level in a test sample that is greater than the standard error of the assay employed to assess expression, and is preferably at least twice, and more preferably three, four, five or ten times the expression level of ZNF365/ZFP365 in a control sample (e.g., sample from a healthy subjects not having ZNF365/ZFP365 associated disease) and preferably, the average expression level of ZNF365/ZFP365 in several control samples. A "significantly lower level of expression" of ZNF365/ZFP365 refers to an expression level in a test sample that is at least twice, and more preferably three, four, five or ten times lower than the expression level of ZNF365/ZFP365 in a control sample (e.g., sample from a healthy subject not having ZNF365/ZFP365 associated disease) and preferably, the average expression level of ZNF365/ZFP365 in several control samples.

An "overexpression" or "significantly higher level of expression or copy number" of a ZNF365/ZFP365 refers to an expression level or copy number in a test sample that is greater than the standard error of the assay employed to assess expression or copy number, and is preferably at least twice, and more preferably three, four, five or ten or more times the expression level or copy number of ZNF365/ZFP365 in a control sample (e.g., sample from a healthy subject not afflicted with cancer) and preferably, the average expression level or copy number of ZNF365/ZFP365 in several control samples.

As used herein, the term "predictive" includes the use of ZNF365/ZFP365 status, e.g., over- or under-activity, emergence, expression, growth, remission, recurrence or resistance of tumors before, during or after therapy, for determining the likelihood of response of a cancer to anti-cancer treatment (e.g., chemotherapy, such as administration of inhibitors of PARP-1, PARP-2, DNA-PK, Ku70, MRE11, RPA, topoisomerases such as TOP2A and TOP2B, and CHEK1; or radiation therapy; or a combination of chemotherapy and radiation therapy.) Such predictive use of ZNF365/ZFP365 may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression (e.g., by ISH, Northern Blot, or qPCR), increased or decreased protein level (e.g., by IHC), or increased or decreased activity (determined by, for example, modulation of a pathway in which ZNF365/ZFP365 is involved), e.g., in more than about 5%, 6%, 7%, 8%, 9%, 10%, 11%, 12%, 13%, 14%, 15%, 20%, 25%, or more of human cancers types or cancer samples; (2) its presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its presence or absence in clinical subset of patients with cancer (e.g., those responding to a particular therapy or those developing resistance).

The term "probe" refers to any molecule which is capable of selectively binding to a specifically intended target molecule, for example, a nucleotide transcript or protein encoded by or corresponding to ZNF365/ZFP365. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules. The term "response to anti-cancer therapy" relates to any response of the hyperproliferative disorder (e.g., cancer) to an anti-cancer therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to ZNF365/ZFP365 measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom ZNF365/ZFP365 measurement values are known. In certain embodiments, the same doses of cancer therapeutic agents are administered to each subject. In related embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. ZNF365/ZFP365 measurement threshold values that correlate to outcome of a cancer therapy can be determined using methods such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

An "RNA interfering agent" as used herein, is defined as any agent which interferes with or inhibits expression of a target gene, e.g., ZNF365/ZFP365 of the invention, by RNA interference (RNAi). Such RNA interfering agents include, but are not limited to, nucleic acid molecules including RNA molecules which are homologous to the target gene, e.g., ZNF365/ZFP365 of the invention, or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., ZNF365/ZFP365 gene of the invention) or protein encoded by the target gene, e.g., ZNF365/ZFP365 protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

The term "sensitize" means to alter cancer cells or tumor cells in a way that allows for more effective treatment of the associated cancer with a cancer therapy (e.g., chemotherapeutic or radiation therapy). In some embodiments, normal cells are not affected to an extent that causes the normal cells to be unduly injured by the cancer therapy (e.g., chemotherapy or radiation therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anticancer agents or chemotherapy drugs can be greater than the sum of the separate effects of the anticancer agents or chemotherapy drugs alone.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated be reference herein).

RNA interfering agents, e.g., siRNA molecules, may be administered to a patient having or at risk for having cancer, to inhibit expression of ZNF365/ZFP365 gene of the invention, e.g., ZNF365/ZFP365 gene which is overexpressed in cancer (such as ZNF365/ZFP365s listed in Table 3) and thereby treat, prevent, or inhibit cancer in the subject.

As used herein, "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of ZNF365/ZFP365 of the invention and normal post-transcriptional processing (e.g. splicing), if any, of the RNA transcript, and reverse transcription of the RNA transcript.

An "underexpression" or "significantly lower level of expression or copy number" of a ZNF365/ZFP365 refers to an expression level or copy number in a test sample that is greater than the standard error of the assay employed to assess expression or copy number, but is preferably at least twice, and more preferably three, four, five or ten or more times less than the expression level or copy number of ZNF365/ZFP365 in a control sample (e.g., sample from a healthy subject not afflicted with cancer) and preferably, the average expression level or copy number of ZNF365/ZFP365 in several control samples.

The term "ZFP365" refers to zinc finger protein 365 and is encoded by the "ZNF365" gene (Gianfrancesco et al. (2003) *Am. J. Hum. Genet.* 72:1479-1491). The term is intended to include fragments, variants (e.g., allelic variants) and derivatives thereof. At least four ZNF365 splice variants encoding four human ZFP365 isoforms exist. The sequence of human ZNF365 transcript variant 1 differs in the 3' coding region and 3' untranslated region (UTR) compared to variant 3 and is available to the public at the GenBank database under NM_014951.2 and NP_055766.2. The resulting protein, ZFP365 isoform A is shorter and has a distinct C-terminus compared to that of ZFP365 isoform C. The sequence of human ZNF365 transcript variant 2 differs in the 3' coding region and 3' UTR compared to variant 3 and is available to the public under NM_199450.2 and NP_955522.1. The resulting protein, ZFP 365 isoform B is shorter and has a distinct C-terminus compared to that of ZFP365 isoform C. The sequence of human ZNF365 transcript variant 3, which encodes the longest of the four human ZFP365 isoforms (i.e., isoform C), can be found under NM_199451.2 and NP_955523.1. The sequence of human ZNF365 transcript variant 4 differs in the 5' coding region and 5' UTR, as well as maintains multiple coding region differences, compared to variant 3 and is available to the public under NM_199452.3 and NP_955524.3. The resulting protein, ZFP365 isoform D, is shorter and has a distinct N-terminus compared to that of ZFP365 isoform C due to a change in the translation initiation site causing an alternate start codon compared to that of ZFP365 isoform C. Nucleic acid and polypeptide sequences of ZNF365/ZFP365 orthologs in organisms other than humans are well known and include, for example, mouse ZNF365/ZFP365 (NM_178679.2 and NP_848794.1), chimpanzee ZNF365/ZFP365 (XM_001165752.1 and XP_001165752.1), rat ZNF365/ZFP365 (NM_001025145.1 and NP_001020316.1), cow ZNF365/ZFP365 (XM_599467.3 and XP_599467.2), dog ZNF365/ZFP365 (XM_546120.2 and XP_546120.2), chicken ZNF365/ZFP365 (XM_421539.2 and XP_421539.2), and zebrafish ZNF365/ZFP365 (XM_001339655.1 and XP_001339691.1). Representative sequences of ZNF365/ZFP365 orthologs are presented below in Table 1. It is to be noted that the term can further be used to refer to any combination of features described herein regarding ZNF365/ZFP365 molecules. For example, any combination of sequence composition, percentage identify, sequence length, domain structure, functional activity, etc. can be used to describe a ZNF365/ZFP365 molecule of the present invention.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |

GENETIC CODE

| | |
|---|---|
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding ZNF365/ZFP365 (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

TABLE 1

```
SEQ ID NO: 1 Human ZFP365 (isoform A) cDNA Sequence
   1    atgcaacaga aggcttttga ggaaagcaga tatccctggc aggagtcctt tgagaatgtt
  61    gctgtgtgcc tgccattacg ctgcccgagg tgtggagacc ataccagatt tagaagcttg
 121    tcatccttga gggcccatct ggagttcagt cacagctacg aagaaagaac cctcttgaca
 181    aaatgcagtc tctttccatc cctcaaagac acagacctag tcacttcctc agaactcctg
 241    aaaccgggaa aattgcagag cagtggcaac gtggtaaagc agaaaccgag ctatgttaac
 301    ttgtacagca tttcacatga acattccaag gacaggaagc catttgaggt ggtggcagag
 361    aggcctgtgt cctatgtgca gacctacact gccatggacc tccatgcaga ctcgctggat
 421    gggacacggt cgggtcctgg actgcccacc tcagacacca aagcttcttt cgaggcacat
 481    gtcagagaaa aattcaatcg aatggttgag gctgtggata ggaccattga agagagaatt
 541    gataaactca ccaaagagtt ggcccagaaa actgcggaac tgttggaagt tcgggcagct
 601    tttgtgcagc tgactcagaa aaagcaggaa gttcagagac gagagcgggc cttaaacaga
 661    caggtggacg tggccgtgga aatgatagct gtactgaggc aacgcctgac ggaatctgag
 721    gaggagcttc ttaggaaaga agaagaagtt gtcacattca accatttcct ggaagcggca
 781    gctgagaagg aggttcaagg gaaagcccgg ctccaggact ttattgagaa tctgttacag
 841    cgggtagaac tggcggagaa gcagcttgag tactatcaga gccagcaggc ctctggcttt
 901    gtccgtgatc tcagcgggca cgtgcttaca gacatctcct caaataggaa gcccaaatgc
 961    ctaagccgag ggcacccgca ttcggtatgt aaccaccctg atctcaaggc ccatttccac
1021    ccaaagggaa ggaaccacct gaaaaaggcc aaggatgaca gagccagcat gcagcctgcc
1081    aaggccattc acgaacaggc tgagtcctca agagacctct gcagacctcc aaagaaaggg
1141    gagctcctgg ggtttggccg caaaggcaac atcaggccca aaatggctaa aaaaaagcca
1201    acagccattg tgaacatcat ctaa SEQ ID NO: 2 Human ZFP365 (isoform A) Amino Acid Sequence
   1    mqqkafeesr ypwqesfenv avclplrcpr cgdhtrfrsl sslrahlefs hsyeertllt
  61    kcslfpslkd tdlvtssell kpgklqssgn vvkqkpsyvn lysishehsk drkpfevvae
 121    rpvsyvqtyt amdlhadsld gtrsgpglpt sdtkasfeah vrekfnrmve avdrtiekri
 181    dkltkelaqk taellevraa fvqltqkkqe vqrreralnr qvdvavemia vlrqrltese
 241    eellrkeeev vtfnhfleaa aekevqgkar lqdfienllq rvelaekqle yyqsqqasgf
 301    vrdlsghvlt dissnrkpkc lsrghphsvc nhpdlkahfh pkgrnhlkka kddrasmqpa
 361    kaiheqaess rdlcrppkkg ellgfgrkgn irpkmakkkp taivnii SEQ ID NO: 3 Human ZFP365 (isoform B) cDNA Sequence
   1    atgcaacaga aggcttttga ggaaagcaga tatccctggc aggagtcctt tgagaatgtt
  61    gctgtgtgcc tgccattacg ctgcccgagg tgtggagacc ataccagatt tagaagcttg
 121    tcatccttga gggcccatct ggagttcagt cacagctacg aagaaagaac cctcttgaca
 181    aaatgcagtc tctttccatc cctcaaagac acagacctag tcacttcctc agaactcctg
 241    aaaccgggaa aattgcagag cagtggcaac gtggtaaagc agaaaccgag ctatgttaac
 301    ttgtacagca tttcacatga acattccaag gacaggaagc catttgaggt ggtggcagag
 361    aggcctgtgt cctatgtgca gacctacact gccatggacc tccatgcaga ctcgctggat
 421    gggacacggt cgggtcctgg actgcccacc tcagacacca aagcttcttt cgaggcacat
 481    gtcagagaaa aattcaatcg aatggttgag gctgtggata ggaccattga agagagaatt
 541    gataaactca ccaaagagtt ggcccagaaa actgcggaac tgttggaagt tcgggcagct
 601    tttgtgcagc tgactcagaa aaagcaggaa gttcagagac gagagcgggc cttaaacaga
 661    caggtggacg tggccgtgga aatgatagct gtactgaggc aacgcctgac ggaatctgag
 721    gaggagcttc ttaggaaaga agaagaagtt gtcacattca accatttcct ggaagcggca
 781    gctgagaagg aggttcaagg gaaagcccgg ctccaggact ttattgagaa tctgttacag
 841    cgggtagaac tggcggagaa gcagcttgag tactatcaga gccagcaggc ctctggcttt
 901    gtccgtgatc tcagcgggca cgtgagctgg aaaggtgctg gcgaagctcg cctggtgtgc
 961    caaaatgacc tggaattgga ggagtctgcg attgtggaat aa
```

TABLE 1-continued

```
SEQ ID NO: 4 Human ZFP365 (isoform B) Amino Acid Sequence
    1  mqqkafeesr ypwqesfenv avclplrcpr cgdhtrfrsl sslrahlefs hsyeertllt
   61  kcslfpslkd tdlvtssell kpgklqssgn vvkqkpsyvn lysishehsk drkpfevvae
  121  rpvsyvqtyt amdlhadsld gtrsgpglpt sdtkasfeah vrekfnrmve avdrtiekri
  181  dkltkelaqk taellevraa fvqltqkkqe vqrreralnr qvdvavemia vlrqrltese
  241  eellrkeeev vtfnhfleaa aekevqgkar lqdfienllq rvelaekqle yyqsqqasgf
  301  vrdlsghvsw kgagearlvc qndleleesa ive SEQ ID NO: 5 Human ZFP365 (isoform C) cDNA Sequence
    1  atgcaacaga aggcttttga ggaaagcaga tatccctggc aggagtcctt tgagaatgtt
   61  gctgtgtgcc tgccattacg ctgcccgagg tgtggagacc ataccagatt tagaagcttg
  121  tcatccttga gggcccatct ggagttcagt cacagctacg aagaaagaac cctcttgaca
  181  aaatgcagtc tctttccatc cctcaaagac acagacctca tcacttcctc agaactcctg
  241  aaaccgggaa aattgcagag cagtggcaac gtggtaaagc agaaaccgag ctatgttaac
  301  ttgtacagca tttcacatga acattccaag gacaggaagc catttgaggt ggtggcagag
  361  aggcctgtgt cctatgtgca gacctacact gccatggacc tccatgcaga ctcgctggat
  421  gggacacggt cgggtcctgg actgcccacc tcagacaaca agcttcttt cgaggcacat
  481  gtcagagaaa aattcaatcg aatggttgag gctgtggata ggaccattga aagagaatt
  541  gataaactca ccaaagagtt ggcccagaaa actgcggaac tgttggaagt tcgggcagct
  601  tttgtgcagc tgactcagaa aaagcaggaa gttcagagac gagagcgggc cttaaacaga
  661  caggtggacg tggccgtgga aatgatagct gtactgaggc aacgcctgac agaatctgag
  721  gaggagcttc ttaggaaaga agaagaagtt gtcacattca accatttcct ggaagcggca
  781  gctgagaagg aggttcaagg gaaagcccgg ctccaggact tattgagaa tctgttacag
  841  cgggtagaac tggcggagaa gcagcttgag tactatcaga gccagcagtc ctctggctt
  901  gtccgtgatc tcagcgggca cgtgagctgg aaaggtgctg gcgaagctcg cctggtgtgc
  961  caaaatgacc tggaattgga gattttggc catataaacc accatcttc ggggttgaaa
 1021  gattctcatt gtctagtttt tctgcaagcc ccacctgtgc cctggatcat tttagccagc
 1081  tttctctgga ttctcggaaa tccctggacg tcttccacgg ctactgcagg atttagccaa
 1141  atttgggtgc tatttccctt ttgtggaggg actttttcac acaatgagaa ggacgtctta
 1201  ggactccagg actttgagag agaaagtgtc tctacaagtc aaagcaggaa tatcagcctt
 1261  cttacactag gacaactcca aaattgtgtg attggcaaat tgacaatcat cgatttgttg
 1321  actgaacacc tgttaggtgt aaggcacggt gtcatatgct tccttgggg cttgccttca
 1381  agcagctaa SEQ ID NO: 6 Human ZFP365 (isoform C) Amino Acid Sequence
    1  mqqkafeesr ypwqesfenv avclplrcpr cgdhtrfrsl sslrahlefs hsyeertllt
   61  kcslfpslkd tdlvtssell kpgklqssgn vvkqkpsyvn lysishehsk drkpfevvae
  121  rpvsyvqtyt amdlhadsld gtrsgpglpt sdtkasfeah vrekfnrmve avdrtiekri
  181  dkltkelaqk taellevraa fvqltqkkqe vqrreralnr qvdvavemia vlrqrltese
  241  eellrkeeev vtfnhfleaa aekevqgkar lqdfienllq rvelaekqle yyqsqqasgf
  301  vrdlsghvsw kgagearlvc qndleleifg hinhhlsglk dshclvflqa ppvpwiilas
  361  flwilgnpwt sstatagfsq iwvlfpfcgg tfhhnekdvl glqdferesv stsqsrnisl
  421  ltlgqlqncv igkltiidll tehllgvrhg vicfpwglps ss SEQ ID NO: 7 Human ZFP365 (isoform D) cDNA Sequence
    1  atgtctgcgc tgggtcagat aaccatcact gtctccaggt gctggaatac agagaggaac
   61  caaacagata aaaatccttg cctgcacgga gcttaccttc agctaaggga gacagtcaaa
  121  aacaagtcaa cacatctaaa aagccactg atgaaacagg ctcccccttg aaagaccat
  181  ctcgccttcc aacctctcca tcctgcagag aggaaaaccc aagtttggcg ttggcagtca
  241  ggtaattcat cagatctgga aaccacctca tcagcatccc cctggccaac tggaagcaac
  301  cgtgacgttg tgctgaatac acttgcagag tcgtgctgtg gtctctccga gctcatcacg
  361  gcacctcct atgcaggagt ttcaattcaa ggatttagcc aaatttgggt gctatttccc
  421  ttttgtggag ggactttttca tcacaatgag aaggacgtct taggactcca ggactttgag
  481  agagaaagtg tctctacaag tcaaagcagg aatatcactt ccttacact aggacaactc
  541  caaaattgtg tgattggcaa attgacaatc atcgatttgt tgactgaaca cctgttaggt
  601  gtaaggcacg gtgtcatatg ctttccttgg ggcttgcctt caagcagcta a SEQ ID NO: 8 Human ZFP365 (isoform D) Amino Acid Sequence
    1  msalgqitit vsrcwntern qtdknpclhg aylqlretvk nksthlkkpl mkqappwkdh
   61  lafqplhpae rktqvwrwqs gnssdletts saspwptgsn rdvvlntlae sccglselit
  121  appyagvsiq gfsqiwvlfp fcggtfhhne kdvlglqdfe resystsqsr nislltlgql
  181  qncvigklti idlltehllg vrhgvicfpw glpsss SEQ ID NO: 9 Mouse ZFP365 cDNA Sequence
    1  atgcaacaga cgactttga ggaaagccgg taccattggc aggactcgct ggagaatgtc
   61  gctgtgtgcc tgccattccg ctgcccgagg tgtggagacc ataccagatt tagaagcttg
  121  tcatccttga gggcccatct ggaattcagt cacagctacg aagagcgaac cctcctgaca
  181  aaatgcagcc tcctgccctc tctcaaggac acagagcttc tcaggtcctc ggaactcccg
  241  aagcaggaa aagtactccg gggccacgca aggtgacca agcagaagtc gagctatgtt
  301  aacttgtaca gcatctccca cgggcactcc aaggacacga acccctttga gatggtggca
  361  gagaggcccg tgtcctatgt gcagacctac acggccgtgg acatccggga tgctcctctg
  421  gatgctccct gcgccagccc tggtctcccc acccaagata ccaaagctgc tttcgaggct
  481  cacgtccgag aaaagttcaa tcgcatggta gaggccgtgg acaggaccat cgagaagaga
  541  atcgacaaac tcaccaaaga gttggcccag aaaaccgccg aactgttgga agtccgggca
  601  gcctttgcgc agctgactca gaagaagcag gaggtccaga gaagagggc ggcctgaac
  661  aaacaggtag atgtggccgt ggaaatgatc gcagtgctga agcacgtct gacgaatcc
  721  gaggaggagc tcctgaggaa agaggaagaa gtcgtcacat tcaaccattt cctggaggca
  781  gcggctgaga aggaggttca ggaaaagcg aggctccagg actttattga aaatctgctg
  841  caacgggtag aattggcgga agcagttg gaatattatc aaagccagca agcctccggt
  901  tttagctgtg acactagtga gcatatgctc acagacatcc catcgaacag gaagcccaga
```

TABLE 1-continued

```
 961  tgcctaagcc gagggcacca gcattctgtt tgcaaccatc ctgagatgag ggcccatttc
1021  catctgaagg ggagaagcta cctgaagaaa gccaaggatg agcgagccgg gatgcagccc
1081  gccaaggcca ttcacgaacc ggctgagtct ccaagagaat tcttcagacc agccaagaaa
1141  ggggaacacc tgggtctgag ccggaaaggg aatttcaggc ccaaaatggc taaaaagaag
1201  cctacagcaa tcgtgaatat catctag SEQ ID NO: 10 Mouse ZFP365 Amino Acid Sequence
   1  mqqttfeesr yhwqdslenv avclpfrcpr cgdhtrfrsl sslrahlefs hsyeertllt
  61  kcsllpslkd tellrsselp kqgkvlrgha kvtkqkssyv nlysishghs kdtkpfemva
 121  erpvsyvqty tavdiradsl dapcaspglp tqdtkaafea hvrekfnrmv eavdrtiekr
 181  idkltkelaq ktaellevra afaqltqkkq evqrreraln kqvdvavemi avlkqrltes
 241  eeellrkeee vvtfnhflea aaekevqgka rlqdfienll qrvelaekql eyyqsqqasg
 301  fscdtsehml tdipsnrkpr clsrghqhsv cnhpemrahf hlkgrsylkk akderagmqp
 361  akaihepaes preffrpakk gehlglsrkg nfrpkmakkk ptaivnii
```

TABLE 2

| Gene Symbol | Gene Name | GenBank Gene Accession Number | GenBank Protein Accession Number | Gene ID |
|---|---|---|---|---|
| PARP-1 | Poly (ADP-ribose) polymerase 1 | e.g., NM_001618.3 and NM_007415.2 | e.g., NP_001609.2 and NP_031441.2 | e.g., 142 and 11545 |
| PARP-2 | Poly (ADP-ribose) polymerase 2 | e.g., NM_005484.3/ NM_001042618.1 and NM_009632.2 | e.g., NP_005475.2/ NP_001036083.1 and NP_033762.1 | e.g., 10038 and 11546 |
| DNA-PK | PRKDC protein kinase, DNA-activated, catalytic polypeptide | e.g., NM_006904.6/NM_001081640.1 and NM_011159.2 | e.g., NP_008835.5/NP_001075109.1 and NP_035289.2 | e.g., 5591 and 19090 |
| Ku70 | X-ray repair complementing defective repair in Chinese hamster cells 6 | e.g., NM_001469.3 and NM_010247.2 | e.g., NP_001460.1 and NP_034377.2 | e.g., 2547 and 14375 |
| MRE11 | Meiotic recombination 11 homolog A | e.g., NM_005590.3/NM_005591.3 and NM_018736.2 | e.g., NP_005581.2/NP_005582.1 and NP_061206.1 | e.g., 4361 and 17535 |
| RPA1 | Replication protein A1, 70 kDa | e.g., NM_002945.3 and NM_001164223.1/NM-026653.2 | e.g., NP_002936.1 and NP_001157695.1/NP_080929.1 | e.g., 6117 and 68275 |
| TOP2A | Topoisomerase (DNA) II alpha 170 kDa | e.g., NM_001067.3 and NM_011623.2 | e.g., NP_001058.2 and NM_035753.2 | e.g., 7153 and 21973 |
| TOP2B | Topoisomerase (DNA) II beta 180 kDa | e.g., NM_001068.2 and NM_009409.2 | e.g., NP_001059.2 and NP_033435.2 | e.g., 7155 and 21974 |
| CHEK1 | CHK1 checkpoint homolog | e.g., NM_001114121.2/NM_001114122.1/ NM_001244846.1/ NM_001274.5 and NM_007691.5 | e.g., NP_001107593.1/NP_001107594.1/ NP_001231775.1/ NP_001265.2 and NP_031717.2 | e.g., 1111 and 12649 |
| BRCA1 | Breast cancer 1, early onset | e.g., NM_007294.3/NM_007297.3/ NM_007298.3/NM_007299.3/ NM_007300.3 and NM_009764.3 | e.g., NP_009225.1/NP_009228.2/ NP_009229.2/NP_009230.2/ NP_009231.2 and NP_033894.3 | e.g., 672 and 12189 |
| BRCA2 | Breast cancer 2, early onset | e.g., NM_000059.3 and NM_001081001.1/NM_009765.2 | e.g., NP_000050.2 and NP_001074470.1/NP_033895.2 | e.g., 675 and 12190 |
| FANCA | Fanconi anemia, complementation group A | e.g., NM_000135.2/NM_001018112.1 and NM_016925.3 | e.g., NP_000126.2/NP_001018122.1 and NP_058621.2 | e.g., 2175 and 14087 |
| FANCB | Fanconi anemia, complementation group B | e.g., NM_001018113.1/NM_152633.2 and NM_001146081.1/NM_175027.4 | NP_001018123.1/NP_689846.1 and NP_001139553.1/NP_778192.3 | e.g., 2187 and 237211 |
| FANCC | Fanconi anemia, complementation group C | e.g., NM_000136.2/NM_001243743.1/ NM_001243744.1 and NM_001042673.1/NM_007985.2 | e.g., NP_000127.2/NP_001230672.1/ NP_001230673.1 and NP_001036138.1/NP_032011.2 | e.g., 2176 and 14088 |
| FANCD2 | Fanconi anemia, complementation group D2 | e.g., NM_001018115.1/NM_033084.3 and NM_001033244.3 | e.g., NP_001018125.1/NP_149075.2 and NP_001028416.2 | e.g., 2177 and 211651 |
| FANCE | Fanconi anemia, complementation group E | e.g., NM_021922.2 and NM_001163819.1/NM_001163820.1 | e.g., NP_068741.1 and NP_001157291.1/NP_001157292.1 | e.g., 2178 and 72775 |
| FANCF | Fanconi anemia, complementation group F | e.g., NM_022725.3 and NM_001115087.1 | e.g., NP_073562.1 and NP_001108559.1 | e.g., 2188 and 10040608 |

TABLE 2-continued

| Gene Symbol | Gene Name | GenBank Gene Accession Number | GenBank Protein Accession Number | Gene ID |
|---|---|---|---|---|
| FANCG | Fanconi anemia, complementation group G | e.g., NM_004629.1 and NM_001163233.1/NM_053081.2 | e.g., NP_004620.1 and NP_001156705.1/NP_444311.1 | e.g., 2189 and 60534 |
| FANCI | Fanconi anemia, complementation group I | e.g., NM_001113378.1/NM_018193.2 and NM_145946.2 | e.g., NP_001106849.1/NP_060663.2 and NP_666058.2 | e.g., 55215 and 208836 |
| FANCJ | BRCA1 interacting protein C-terminal helicase 1 | e.g., NM_032043.2 and NM_178309.2 | e.g., NP_114432.2 and NP_840094.1 | e.g., 83990 and 237911 |
| FANCL | Fanconi anemia, complementation group L | e.g., NM_001114636.1/NM_018062.3 and NM_025923.2 | e.g., NP_001108108.1/NP_060532.2 and NP_080199.1 | e.g., 55120 and 67030 |
| FANCM | Fanconi anemia, complementation group M | e.g., NM_020937.2 and NM_178912.3 | e.g., NP_065988.1 and NP_849243.2 | e.g., 57697 and 104806 |
| FANCN | Partner and localizer of BRCA2 | e.g., NM_024675.3 and NM_001081238.1 | e.g., NP_078951.2 and NP_001074707.1 | e.g., 79728 and 233826 |

II. Description

A. Subjects

In one embodiment, the subject for whom predicted likelihood of efficacy of an anti-cancer therapy is determined, is a mammal (e.g., mouse, rat, primate, non-human mammal, domestic animal such as dog, cat, cow, horse), and is preferably a human.

In another embodiment of the methods of the invention, the subject has not undergone chemotherapy or radiation therapy. In still another embodiment, the subject has undergone chemotherapy or radiation therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the invention can be used to determine the responsiveness to anti-cancer therapies of many different cancers in subjects. Specific examples of types of cancers for which the phenotype can be determined by the methods encompassed by the invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the cancer whose phenotype is determined by the method of the invention is an epithelial cancer such as, but not limited to, brain cancer (e.g., glioblastomas) bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostrate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated.

B. Sample Collection, Preparation and Separation

In some embodiments, ZNF365/ZFP365 amount and/or activity measurement(s) in a sample from a subject is compared to a predetermined control (standard) sample. The sample from the subject is typically from a diseased tissue, such as cancer cells or tissues. The control sample can be from the same patient or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the ZNF365/ZFP365 amount and/or activity measurement(s) from a subject is compared to a pre-determined level. This pre-determined level is typically obtained from normal samples. As described herein, a "predetermined" ZNF365/ZFP365 amount and/or activity measurement(s) may be a ZNF365/ZFP365 amount and/or activity measurement(s) used to, by way of example only, evaluate a subject that may be selected for treatment, evaluate a response to an anti-cancer therapy, and/or evaluate a response to a combination anti-cancer therapy. A pre-determined ZNF365/ZFP365 amount and/or activity measurement(s) may be determined in populations of patients with or without cancer. The pre-determined ZNF365/ZFP365 amount and/or activity measurement(s) can be a single number, equally applicable to every patient, or the predetermined ZNF365/ZFP365 amount and/or activity measurement(s) can vary according to specific subpopulations of patients. Age, weight, height, and other factors of a subject may affect the pre-determined ZNF365/ZFP365 amount and/or activity measurement(s) of the individual. Furthermore, the pre-determined ZNF365/ZFP365 amount and/or activity can be determined for each subject individually. The pre-determined ZNF365/ZFP365 amount and/or activity measurement(s) can be any suitable standard. For example, the pre-determined ZNF365/ZFP365 amount and/or activity measurement(s) can be obtained from the same or a different human for whom a patient selection is being assessed. In one embodiment, the pre-determined ZNF365/ZFP365 amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of ZNF365/ZFP365 amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in ZNF365/ZFP365 amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the ZNF365/ZFP365 amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of ZNF365/ZFP365 measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transportions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (LIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (LIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

C. ZNF365/ZFP365 Nucleic Acids and Polypeptides

As used herein, the ZNF365 gene or a fragment thereof, e.g., a biologically active fragment thereof, as well as to the detection of expression and/or activity of gene products encoded by the ZNF365 gene (i.e., a "ZNF365 gene product" or "ZFP365") or fragments thereof, e.g., biologically active fragments thereof, including sequences, splice variants, isoforms, and structures, have been described in the art.

One aspect of the invention pertains to the use of isolated nucleic acid molecules that correspond to ZNF365, including nucleic acids which encode a polypeptide corresponding to ZFP365 or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A ZNF365 nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a ZNF365 nucleic acid sequence. Probes based on the sequence of a ZNF365 nucleic acid molecule can be used to detect transcripts or genomic sequences corresponding to one or more markers of the invention. The probe comprises a label group attached thereto, e.g., a radioisotope, a fluorescent compound, an enzyme, or an enzyme co-factor.

ZNF365 nucleic acid molecules that differ, due to degeneracy of the genetic code, from the nucleotide sequence of nucleic acid molecules encoding a protein which corresponds to ZFP365, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, ZNF365 alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $1/100$ or $1/1000$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the invention or to a nucleic acid molecule encoding a protein corresponding to a marker of the invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of Current Protocols in Molecular Biology, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, a ZFP365 protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a ZFP365 protein described herein.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-ZNF365 antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid molecule of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the invention pertains to the use of ZFP365 proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a ZFP365 polypeptide include polypeptides comprising amino acid sequences sufficiently identical to or derived from a ZFP365 amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have an amino acid sequence of a ZFP365 protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a marker of the invention. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence, immunoglobulin fusion protein, toxin, or other useful protein sequence. Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to ZFP365 variants of the polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198: 1056; Ike et al., 1983 *Nucleic Acid Res.* 11:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

The production and use of ZNF365 nucleic acid and/or ZFP365 polypeptide molecules described herein can be facilitated by using standard recombinant techniques. In some embodiments, such techniques use vectors, preferably expression vectors, containing a nucleic acid encoding a ZFP365 polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors for use in the invention can be designed for expression of a polypeptide corresponding to a marker of the invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expres-* sion *Technology: Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell. Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

D. Analyzing ZNF365/ZFP365

ZNF365 nucleic acids and/or ZFP365 polypeptides can be analyzed according to the methods described herein and techniques known to the skilled artisan to identify such genetic alterations useful for the present invention including, but not limited to, 1) a deletion of one or more nucleotides from a ZNF365 gene, 2) an addition of one or more nucleotides to a ZNF365 gene, 3) a substitution of one or more nucleotides of a ZNF365 gene, 4) a chromosomal rearrangement of a ZNF365 gene, 5) an alteration in the level of a messenger RNA transcript of a ZNF365 gene, 6) aberrant modification of a ZNF365 gene, such as of the methylation pattern of the genomic DNA, 7) the presence of a non-wild type splicing pattern of a messenger RNA transcript of a ZNF365 gene, 8) a non-wild type level of a ZFP365 polypeptide, 9) allelic loss or gain of a ZNF365 gene, and 10) inappropriate post-translational modification of a ZFP365 polypeptide.

1. Methods for Detection of Copy Number

Methods of evaluating the copy number of ZNF365 are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of anticancer treatment.

Methods of evaluating the copy number of ZNF365 loci include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the ZNF365 copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl. Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

2. Methods for Detection of ZNF365 Gene Expression

ZNF365 expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA or microRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of ZNF365/ZFP365 and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising of ZNF365/ZFP365 DNA. Positive hybridization signal is obtained with the sample containing ZNF365/ZFP365 transcripts. Methods of preparing DNA arrays and their use are well known in the art (see, e.g., U.S. Pat. Nos. 6,618,6796; 6,379,897; 6,664,377; 6,451,536; 548, 257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

3. Methods for Detection of ZFP365 Expression

The activity or level of a ZFP 365 protein can be detected and/or quantified by detecting or quantifying the expressed polypeptide. The polypeptide can be detected and quantified by any of a number of means well known to those of skill in the art. Aberrant levels of polypeptide expression of the polypeptides encoded by ZNF365/ZFP365 and functionally similar homologs thereof, including a fragment or genetic alteration thereof (e.g., in regulatory or promoter regions thereof) are associated with the likelihood of response of a cancer to an anti-cancer therapy. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Ten, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired ZFP365 standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, ZFP365 in the sample is allowed to react with the corresponding immobilized antibody, radioisotope- or enzyme-labeled anti-ZFP365 antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring ZFP365 levels comprises the steps of: contacting a biological specimen with an antibody or variant (e.g., fragment) thereof which selectively binds ZFP365, and detecting whether said antibody or variant thereof is bound to said sample and thereby measuring the levels of ZFP365.

Enzymatic and radiolabeling of ZFP365 and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect ZFP365 according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-ZNF365/ZFP365 antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of ZFP365, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-ZFP365 antibodies, such as intrabodies, may also be used for imaging purposes, for example, to detect the presence of ZFP365 in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99m}$Tc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain ZFP365. The labeled antibody or antibody fragment can then be detected using known techniques.

Antibodies that may be used to detect ZFP365 include any antibody, whether natural or synthetic, full length or a fragment thereof, monoclonal or polyclonal, that binds sufficiently strongly and specifically to the ZNF365/ZFP365 polypeptide to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to ZFP365 relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., ZFP365 binding fragments, of antibodies. For example, antibody fragments capable of binding to ZFP365 or portions thereof, including, but not limited to, Fv, Fab, Fab' and F (ab') 2 fragments can be used. Such fragments can be produced by enzymatic cleavage or by recombinant techniques. For example, papain or pepsin cleavage can generate Fab or F (ab') 2 fragments, respectively. Other proteases with the requisite substrate specificity can also be used to generate Fab or F (ab') 2 fragments. Antibodies can also be produced in a variety of truncated forms using antibody genes in which one or more stop codons have been introduced upstream of the natural stop site. For example, a chimeric gene encoding a F (ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to ZFP365 other than antibodies are used, such as peptides. Peptides that specifically bind to ZFP365 can be identified by any means known in the art. For example, specific peptide binders of ZFP365 can be screened for using peptide phage display libraries.

In addition, the ZFP365 protein may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) Tibtech 18, 151-160; Rowley et al. (2000) Methods 20, 383-397; Kuster and Mann (1998) Curr. Opin. Structural Biol. 8, 393-400). Further, mass spectrometric techniques have been developed that permit at least partial de novo sequencing of isolated proteins (see, e.g., Chait et al. (1993) Science 262, 89-92; Keough et al. (1999) Proc. Natl. Acad. Sci. USA. 96, 7131-7136; reviewed in Bergman (2000) EXS 88, 133-44).

In certain embodiments, a gas phase ion spectrophotometer is used. In other embodiments, laser-desorption/ionization mass spectrometry is used to analyze the sample. Modem laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes (see, e.g., Hellenkamp et al., U.S. Pat. No. 5,118,937 and Beavis and Chait, U.S. Pat. No. 5,045,694).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied (see, e.g., Hutchens and Yip, U.S. Pat. No. 5,719,060 and Hutchens and Yip, WO 98/59361). The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of a marker or other substances will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually or by computer analysis) to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to be mixed with the known control sample in the same mass spectrometry run.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantification of the amount of the biomolecule present in the first sample. In certain embodiments, the identity of the biomolecules in the first and second sample can also be determined.

4. Methods for Detection of ZNF365/ZFP365 Structural Alterations

The following illustrative methods can be used to identify the presence of a structural alteration in a ZNF365 nucleic acid and/or ZFP365 polypeptide molecule.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a ZNF365 gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a ZNF365 gene under conditions such that hybridization and amplification of the ZNF365 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a ZNF365/ZFP365 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in ZNF365 can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in ZNF365/ZFP365 can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such genetic mutations in ZNF365 can be identified in a variety of contexts, including, for example, germline and somatic mutations.

In yet another embodiment, any of a variety of sequencing reactions known in the art can be used to directly sequence the ZNF365 gene and detect mutations by comparing the sequence of the sample ZNF365 with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad. Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the ZNF365 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type ZNF365 sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in ZNF365 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a ZNF365 sequence, e.g., a wild-type ZNF365 sequence, is hybridized to a cDNA or other DNA product from a test cell(s). The duplex is treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility will be used to identify mutations in ZNF365 genes. For example, single strand conformation polymorphism (SSCP) may be used to detect differences in electrophoretic mobility between mutant and wild type nucleic acids (Orita et al. (1989) Proc Natl. Acad. Sci. USA 86:2766; see also Cotton (1993) Mutat. Res. 285:125-144 and Hayashi (1992) Genet. Anal. Tech. Appl. 9:73-79). Single-stranded DNA fragments of sample and control ZNF365/ZFP365 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell. Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

E. Anti-Cancer Therapeutic Agents

The efficacy of anti-cancer therapies which damage DNA, as well as agents that take advantage of DNA repair defects but do not damage DNA themselves, such as poly ADP ribose polymerase (PARP) inhibitors, as well as other forms of chemotherapy, gene therapy, and radiation therapy, is predicted according to ZNF365/ZFP365 amount and/or activity of a cancer in a subject according to the methods described herein.

In one embodiment, the efficacy of chemotherapies is predicted. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V.

J. et.al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, the efficacy of radiation therapy is predicted. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, the efficacy of other therapies, including gene therapy, is predicted. Examples of such therapies include immunotherapy and hormone therapy. Such therapies include, but are not limited to, the use of antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, oncogenes, growth factor genes, growth factor receptor genes, cell cycle genes, DNA repair genes, and others, may be used in such therapies.

Immunotherapy may comprise, for example, use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

Gene therapy agents generally involve the insertion of copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present invention. For example, gene therapy treatments can comprise administration of expression vectors to enforce exogenous expression of ZFP365 according to the methods and compositions described herein.

In one embodiment, anti-cancer therapy used for cancers whose phenotype is determined by the methods of the invention can comprise one or more types of therapies described herein including, but not limited to, chemotherapeutic agents, immunotherapeutics, anti-angiogenic agents, cytokines, hormones, antibodies, polynucleotides, radiation and photodynamic therapeutic agents. For example, combination therapies can comprise one or more chemotherapeutic agents and radiation, one or more chemotherapeutic agents and immunotherapy, or one or more chemotherapeutic agents, radiation and chemotherapy.

In one embodiment, cancer therapy used for cancers whose phenotype is determined by the methods of the invention can comprise one or more types of therapies described herein including, but not limited to, chemotherapeutic agents, immunotherapeutics, anti-angiogenic agents, cytokines, hormones, antibodies, polynucleotides, radiation and photodynamic therapeutic agents. For example, combination therapies can comprise one or more chemotherapeutic agents and radiation, one or more chemotherapeutic agents and immunotherapy, or one or more chemotherapeutic agents, radiation and chemotherapy.

Hyperthermia, a procedure in which body tissue is exposed to high temperatures (up to 106° F.), is under investigation to assess its effectiveness in the treatment of cancer. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness.

Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

Photodynamic therapy (also called PDT, photoradiation therapy, phototherapy, or photochemotherapy) is a treatment for some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

Laser therapy involves the use of high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser— This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777, 127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth,; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant ZNF365/ZFP365 polypeptides, and fragments thereof, can be administered to subjects. In some embodiments, fusion proteins can be constructed and administered which have enhanced biological properties. In addition, the ZNF365/ZFP365 polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

F. Clincal Efficacy

Clinical efficacy can be measured by any method known in the art. For example, the response to anti-cancer therapies relates to any response of the tumor to chemotherapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., J. Clin. Oncol. (2007) 25:4414-4422) or Miller-Payne score (Ogston et al., Breast (Edinburgh, Scotland) (2003) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-cancer therapeutic regimen is at least 25%, 30%, 35%, 40%, 45%, 50%, 55%, 60%, 65%, 70%, 75%, 80%, 85%, or more.

Additional criteria for evaluating the response to anti-cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to ZNF365/ZFP365 measurements that were determined prior to administration of any anti-cancer therapy. The outcome measurement may be pathologic response to therapy given in the neoadjuvant setting. Alternatively, outcome measures, such as overall survival and disease-free survival can be monitored over a period of time for subjects following anti-cancer therapy for whom ZNF365/ZFP365 measurement values are known. In certain embodiments, the same doses of anti-cancer agents are administered to each subject. In related embodiments, the doses administered are standard doses known in the art for anti-cancer agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. ZNF365/ZFP365 measurement threshold values that correlate to outcome of an anti-cancer therapy can be determined using methods such as those described in the Examples section.

G. Pharmaceutical Compositions

In another aspect, the present invention provides pharmaceutically acceptable compositions which comprise a therapeutically-effective amount of an agent that modulates (e.g., increases or decreases) ZNF365/ZFP365 expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) ZNF365/ZFP365 expression and/or activity, or expression and/or activity of the complex, or composition comprising an agent that modulates (e.g., inhibits) ZNF365/ZFP365 expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) ZNF365/ZFP365 expression and/or activity, or expression and/or activity of the complex encompassed by the invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) ZNF365/ZFP365 expression and/or activity, or expression and/or activity of the complex. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) ZNF365/ZFP365 expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) ZNF365/ZFP365 expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) ZNF365/ZFP365 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) ZNF365/ZFP365 expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) ZNF365/ZFP365 expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Other embodiments of the present invention are described in the following Examples. The present invention is further illustrated by the following examples which should not be construed as further limiting.

EXAMPLES

Example 1

Human ZNF365 is Expressed as Several Splice Variants and Isoforms

Figure 2:
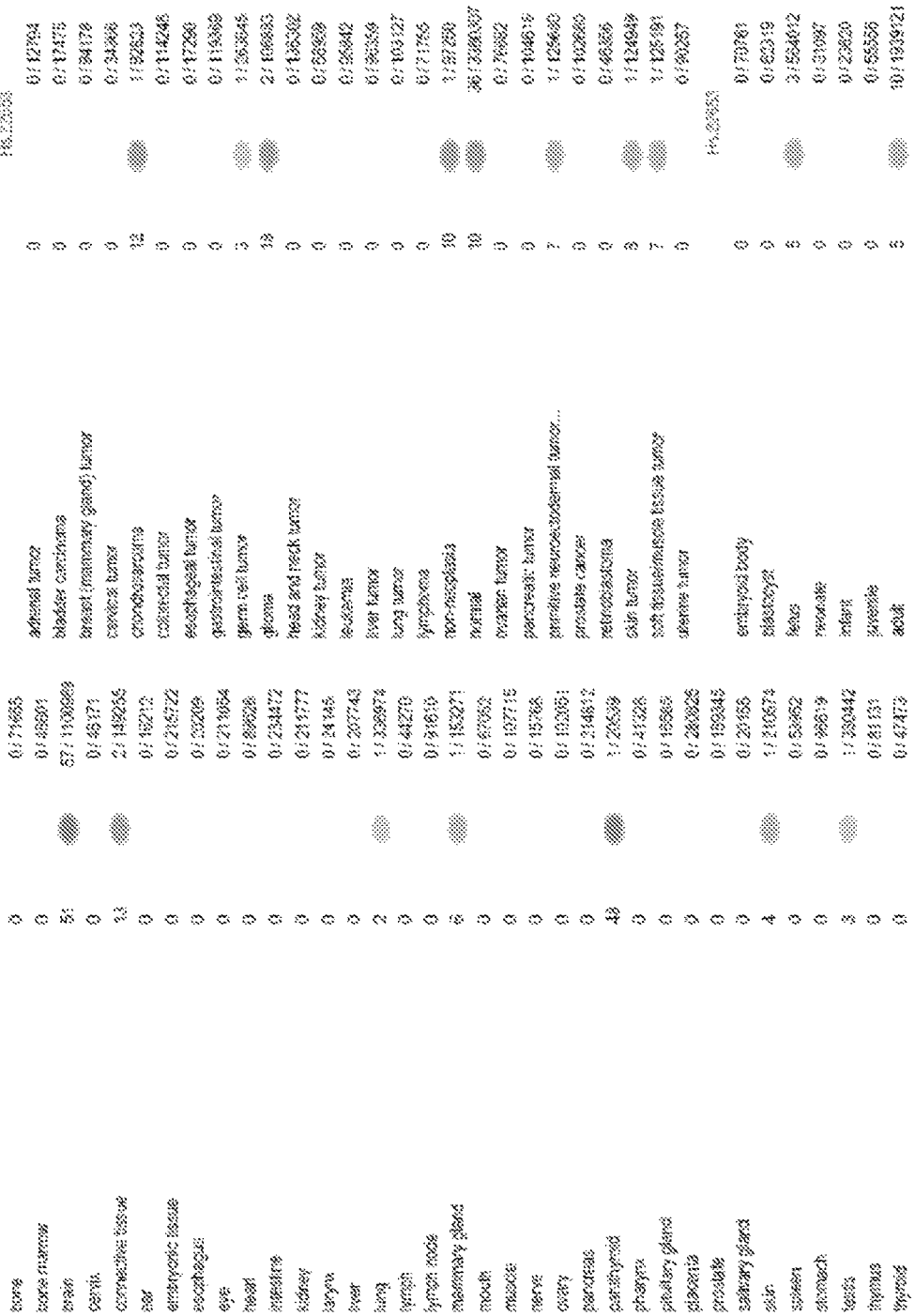
FIG. 2 shows an electronic Northern blot of human ZNF365 transcript expression in various human tissues.

In humans, ZNF365 is differentially expressed in different tissue types according to different protein isoforms generated from several different splice variants shown in FIG. 1. For example, GenBank Accession NM_014951.2 encodes ZNF365 isoform A having a sequence accessible under GenBank Accession NP_055766.2. ZNF365 isoform A is expressed at high levels in the brain, lung, and pancreas. GenBank Accession NM_199450.2 encodes ZNF365 isoform B having a sequence accessible under GenBank Accession NP_955522.1. ZNF365 isoform B is expressed in the placenta. GenBank Accession NM_199451.2 encodes ZNF365 isoform C having a sequence accessible under GenBank Accession NP_955523.1. ZNF365 isoform C is expressed in the kidney and pancreas. GenBank Accession NM_199451.3 encodes ZNF365 isoform D having a sequence accessible under GenBank Accession NP_955524.3. ZNF365 isoform D is expressed ubiquitously at low levels. FIG. 2 shows an electronic Northern blot of human ZNF365 transcript expression in various human tissues. For the shown set of non-fetal normal and cancer human tissues, NCBI's Unigene dataset (Hs.data) was mined for information about the number of unique clones per human ZNF365 gene (NCBI Accession Hs.22653) per tissue. Clones were assigned to particular tissues by applying data-mining heuristics to Unigene's library information file (Hs.lib.info). Electronic expression results were calculated by dividing the number of clones per gene by the number of clones per tissue. They were then normalized by multiplying by 1M, and the obtained normalized counts are presented on the same root scale as the experimental tissue vectors. In addition, the amino acid sequences of the various human ZNF365 protein isoforms are shown in FIG. 3.

Example 2

Figure 5:
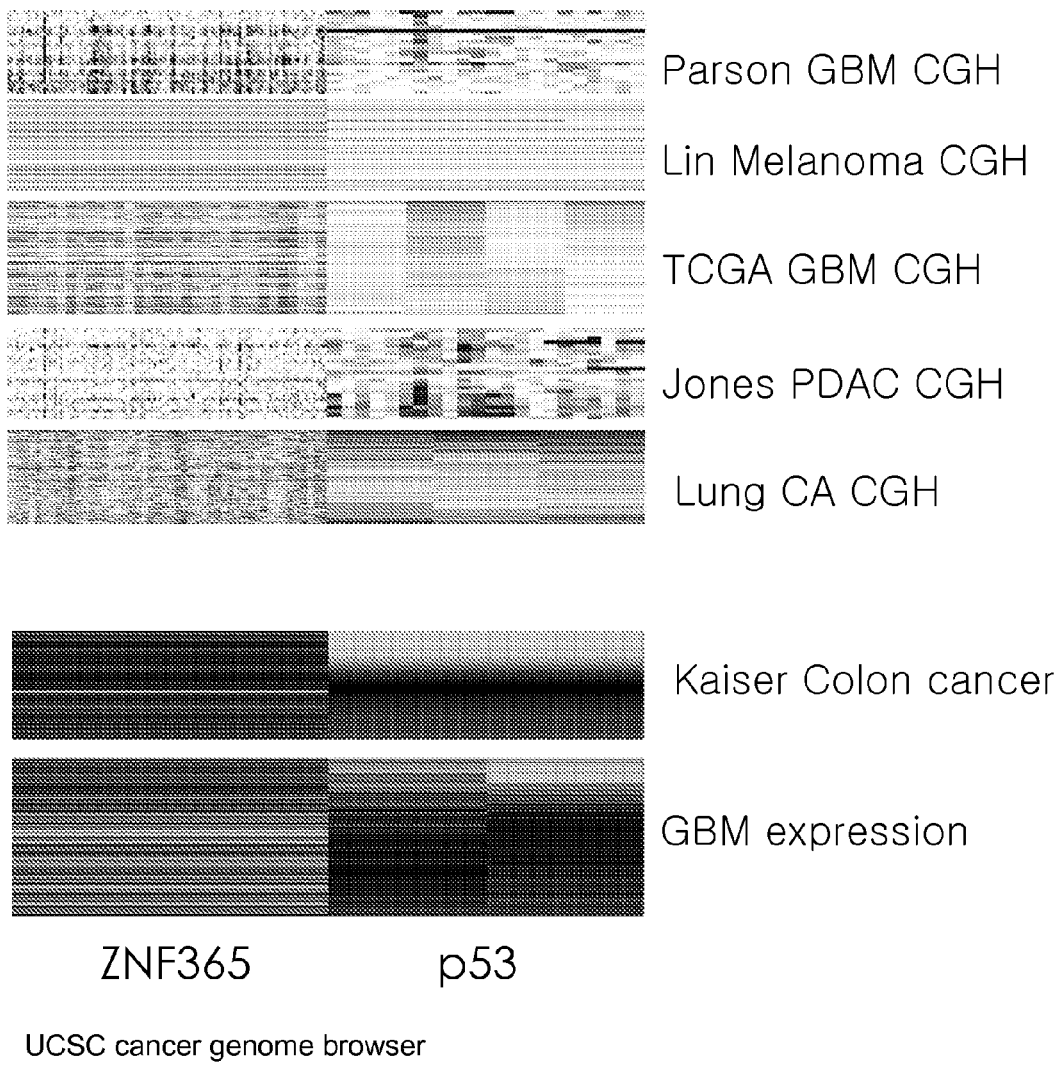
FIG. 5 shows a strong inverse correlation between ZNF365 and p53 expression.

ZNF365 is Strongly Induced Upon p53 Activation in Cells with Telomere-dysfunction and Genomic Instability In a screen to identify genes induced upon p53 activation in mouse cells having telomere-dysfunction and genomic instability, mouse Zfp365 was among the most induced genes based upon p-value. Zfp365 is the mouse ortholog of human ZNF365, as shown in FIG. 4. An analysis of frequent copy number alterations in multiple human cancers assessed using comparative genomic hybridization (CGH), as well as an analysis of ZNF365 mRNA in colon and glioblastoma multiforme (GBM) cancers indicates that ZNF365 expression is strongly inversely correlated with p53 expression (FIG. 5). Deregulation of ZNF365 expression has also been observed in samples from multiple glioblastoma patients.

Example 3

Figure 6:
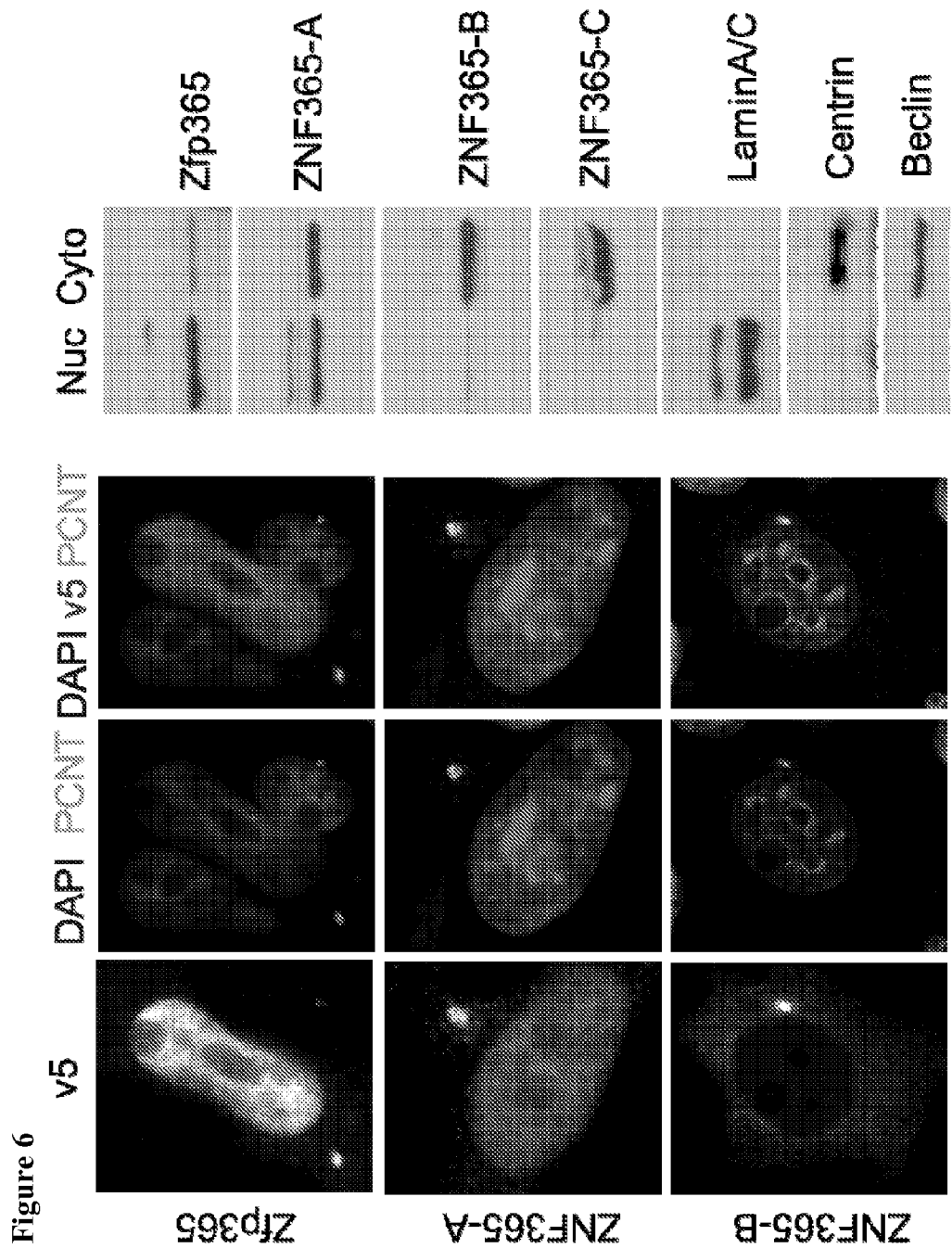
FIG. 6 shows the subcellular localization of ZNF365/ZFP365.
Figure 7:
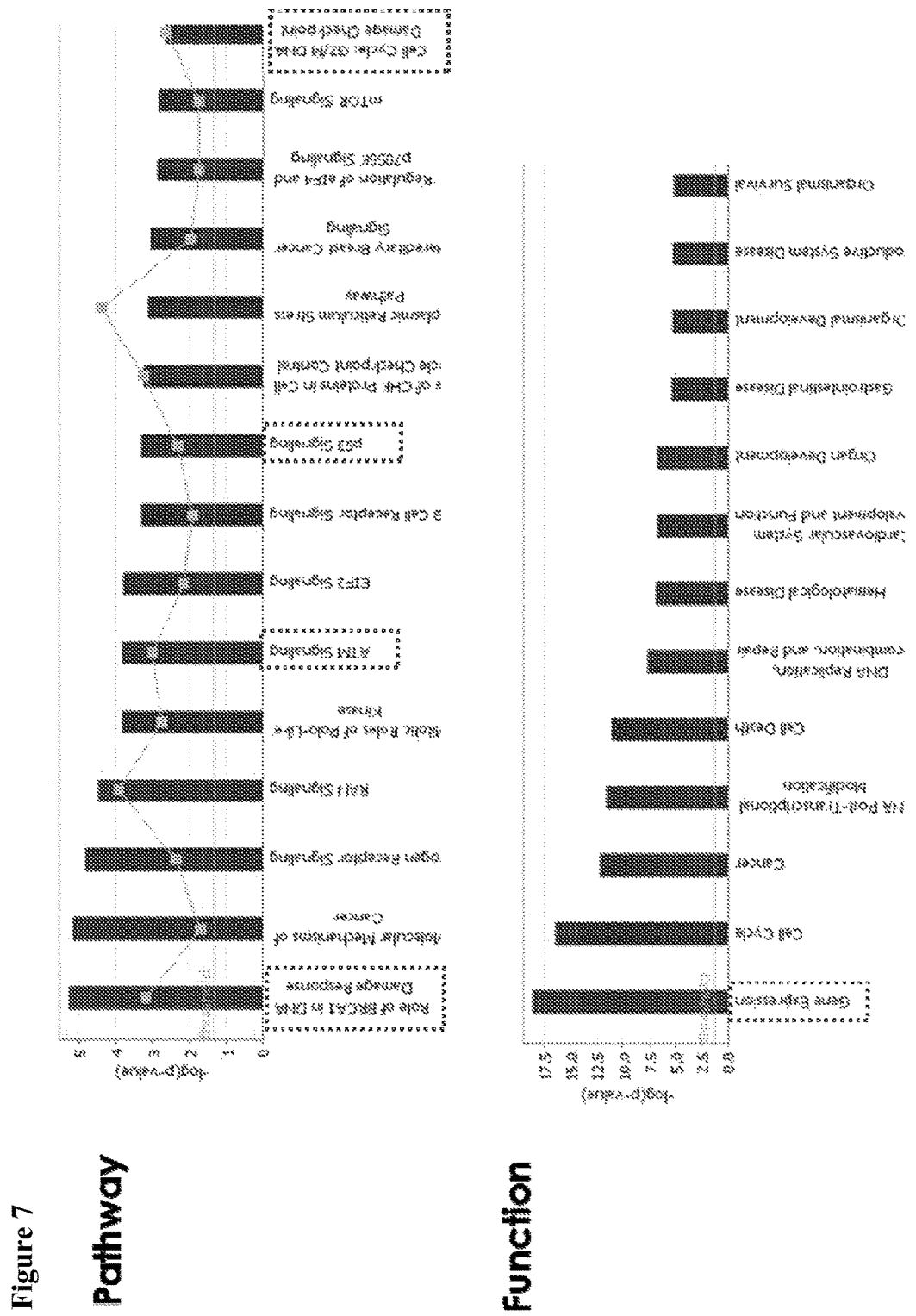
FIG. 7 shows the results of Zfp365 transcriptome-pathway analysis of gene expression profiles generated from HEK-293 cells having enforced Zfp365 expression.

ZNF365/ZFP365 Induces DNA Damage Signaling Pathways Consistent with its Subcellular Localization to the Nucleus and Centrosomes within the Cytoplasm V5-tagged Zfp365 or ZNF365 isoforms expressed in HEK-293 cells showed distribution to both the nucleus (Nuc) and centrosomes in the cytoplasmic compartment (Cyto) (FIG. 6). Transcript ZNF365-A showed similar localization to Zfp365, wherein transcript ZNF365-B primarily localizes to pericentrin (PCNT)-positive centrosomes (FIG. 6). Lamin A/C and beclin staining are shown in FIG. 6 to demarcate nuclear and cytoplasmic fractionation, respectively. Centrin staining is shown in FIG. 6 to demarcate centrosomal fractionation. Consistent with this subcellular localization profile, Zfp365 transcriptome-pathway analyses of gene expression profiles generated from HEK-293 cells having enforced Zfp365 expression indicated that Zfp365 functions to regulate the p53/ATM/DNA damage signaling pathway by functioning as a gene expression regulator (FIG. 7).

Example 4

ZFP365 Interacts with PARP1, DNA-PK, Ku70, and MRE11

Figure 8:
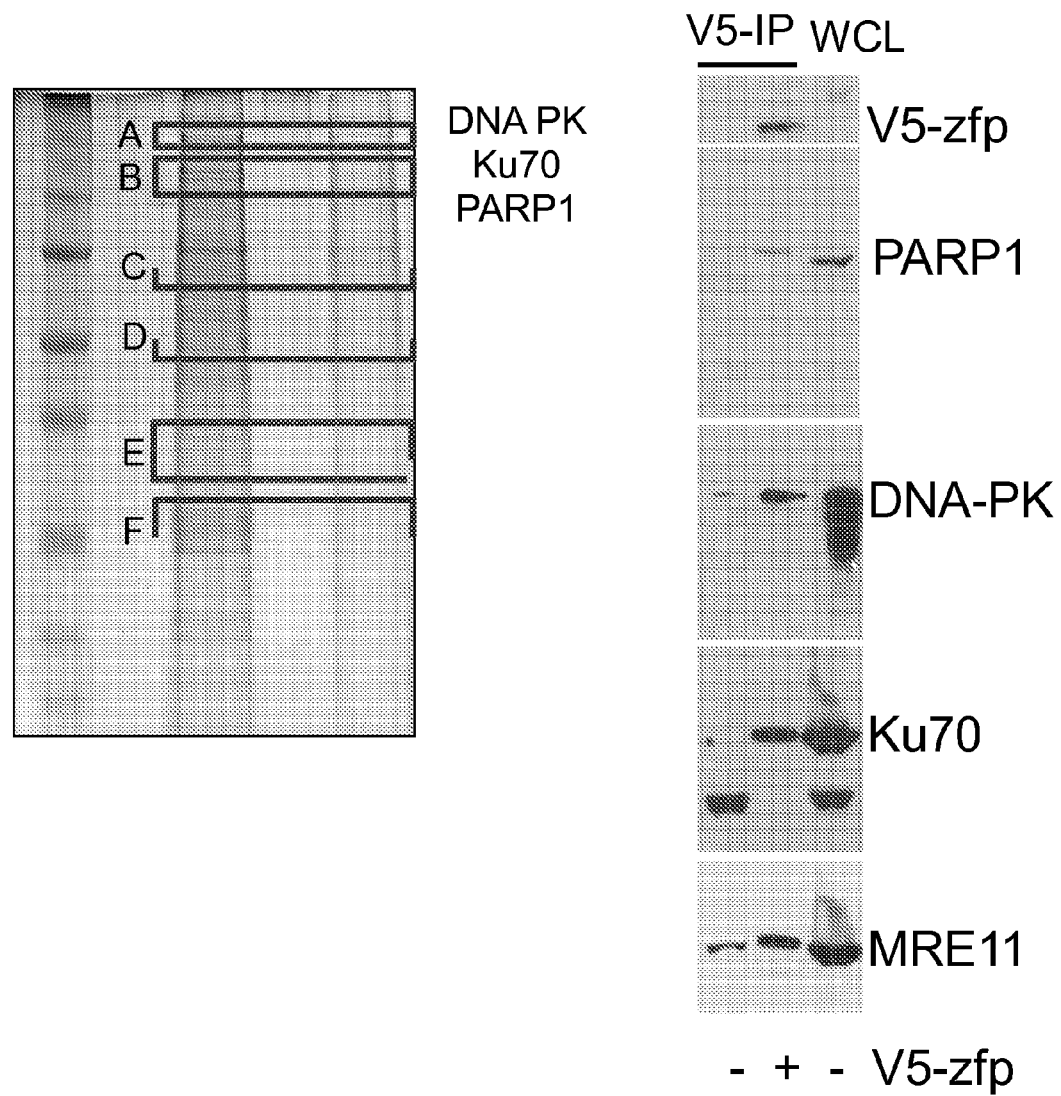
FIG. 8 shows that ZFP365 interacts with PARP1, DNA-PK, Ku70, and MRE11.

In order to identify interacting protein partners of Zfp365, total cellular protein pulled-down by immunohistochemical methods targeting Zfp365 was separated by gel electrophoresis and silver stained (FIG. 8, left panel). Protein bands of interest were extracted and subjected to mass spectrometry analysis. Co-immunoprecipitation experiments using VS-tagged Zfp365 protein confirmed the mass spectrometry analyses indicating interactions between Zfp365 and PARP1, DNA-PK, Ku70, and MRE11 (FIG. 8, right panel). Additionally, Zfp interacts with RPA and topoisomerases.

Example 5

ZNF365 Protects Cells Against DNA Damage

Figure 9:
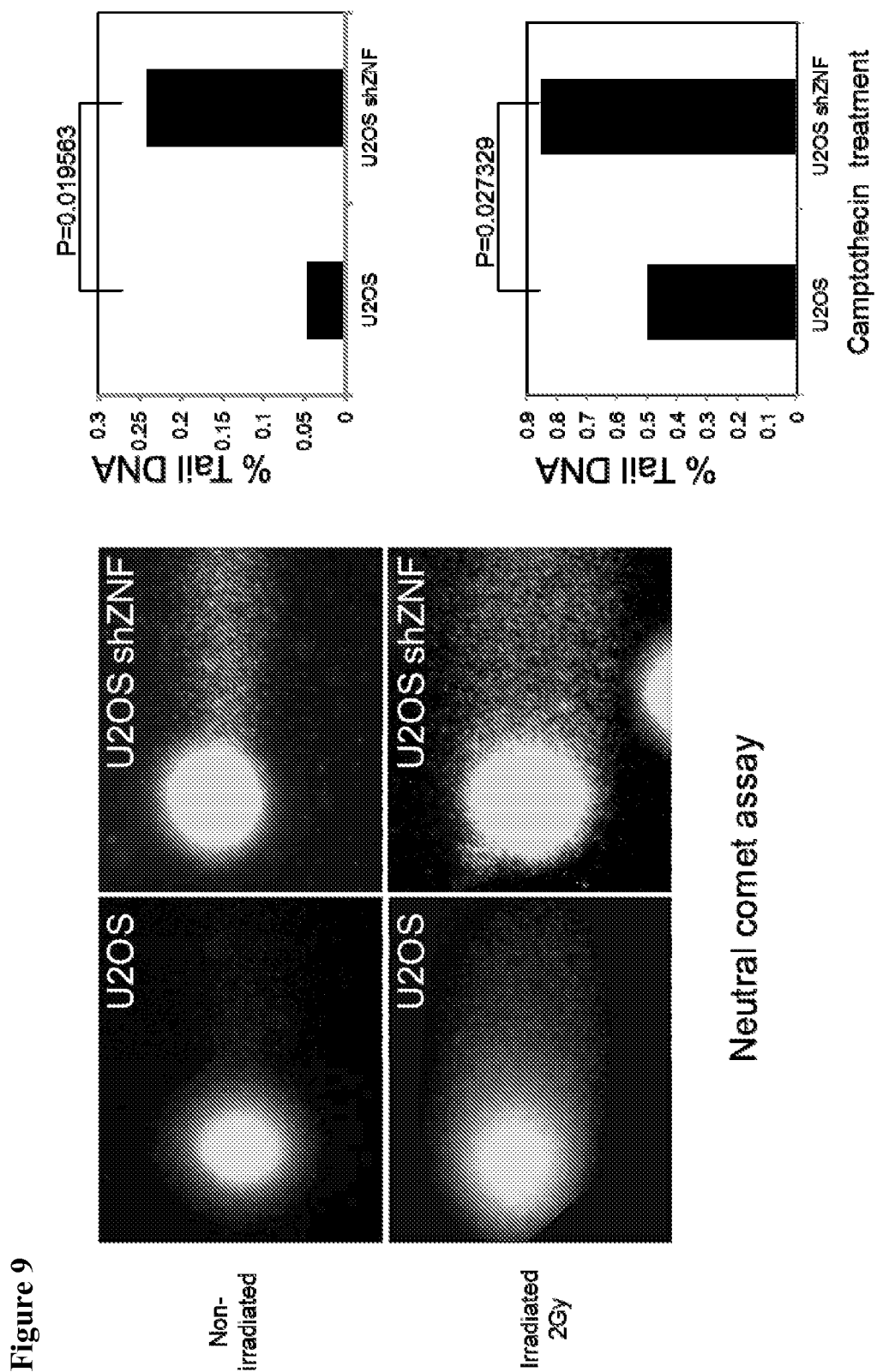
FIG. 9 shows the results of neutral comet assays demonstrating that ZNF365 protects cells against DNA damage.

Cells of the U2OS-p53 wild type osteocaroma cell line express high levels of ZNF365-A. Stable U2OS cells expressing shRNAs targeting ZNF365 (shZNF365) and control U2OS cells were gamma-irradiated at 2 Gy (FIG. 9, left panel) or treated with 1 µM camptothecin (CPT) for 30 min. (FIG. 9, right panel). Cells were then collected and subjected to a neutral comet assay. Quantification of the tail percentages resulting from at least 50 cells scored for each sample for each experiment to calculate the mean DNA tail percentage ($p<0.05$; one-tail Student's t-test) showed that ZNF365 protected against DNA damage (FIG. 9, right panel). All experiments were repeated three to four times.

Figure 10:
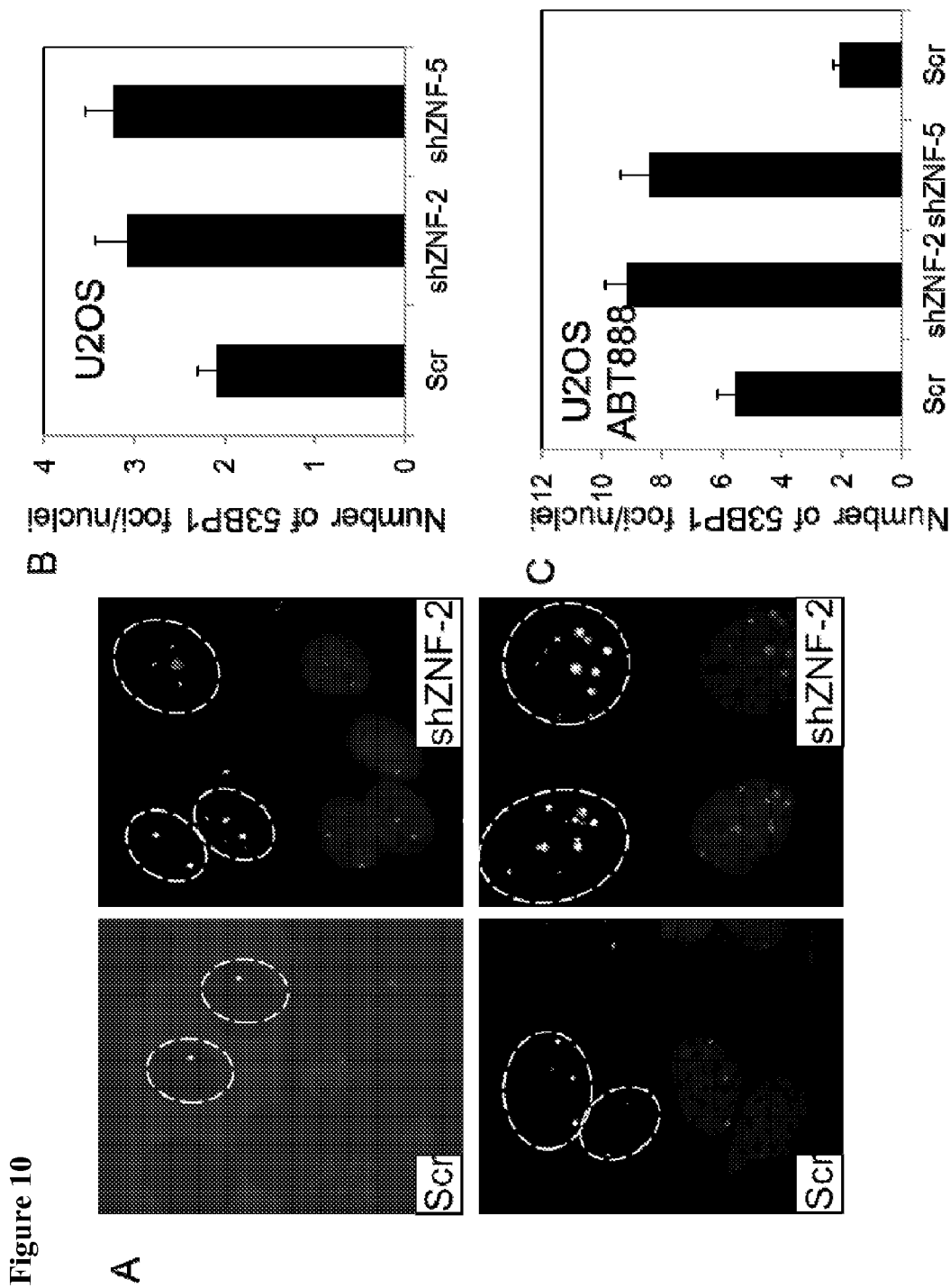
FIGS. 10A-10C show increased DNA double strand breaks (DSB) in ZNF365-deficient cells.

In addition, increased numbers of DNA double strand breaks (DSB) were observed in ZNF365-deficient cells. U2OS cells infected with either a control scrambled shRNA (Scr) to establish the basal DSB levels or with either of two independent shRNA sequences targeting ZNF365 (shZNF-2 or shZNF-5) were scored for 53BP1-positive damage foci as an indicator of DSB (FIG. 10A; red highlighted dots indicates foci and dotted circles indicate nuclei). Quantification of the 53BP1-positive foci indicated increased numbers of DSB in ZNF365-deficient cells (FIG. 10B). In addition, the 53BP1-positive foci in these increased became more prominent upon additional treatment with the PARP inhibitor, ABT888 (FIG. 10C).

Example 6

Figure 11:
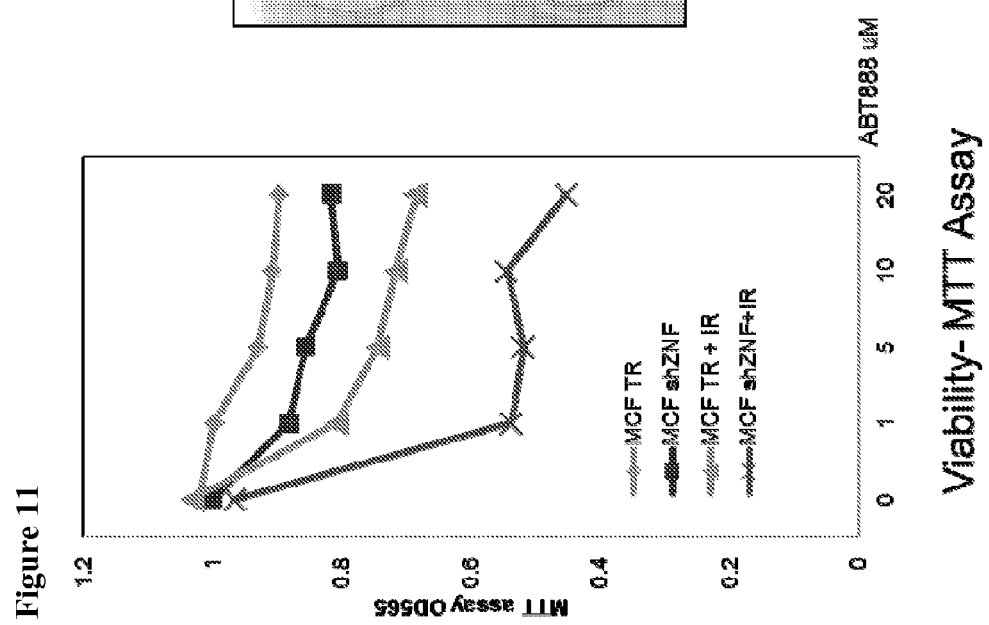
FIG. 11 shows the results of MTT cell proliferation assays of MCF7 breast cancer cells treated with shRNAs targeting ZNF365 (shZNF), treated with irradiation, or treated with a combination of shZNF and irradiation.

ZNF365 Deficiency Sensitizes Cells to Anti-cancer Therapies, Including PARP Inhibitor and Irradiation Therapies, and Impairs Homologous Recombination-mediated DNA Repair Control cells of the MCF7 breast cancer cell line (TR), as well as MCF7 cells transfected with shRNAs targeting ZNF365 (shZNF) were treated with different doses of the PARP inhibitor, ABT888, for 48 hours with or without radiation (2 Gy). A standard MTT cell proliferation assay was performed to determine cell viability. FIG. 11 demonstrates that ZNF365 deficiency sensitizes cells to both anti-cancer treatment using PARP inhibitors and/or irradiation.

Figure 12:
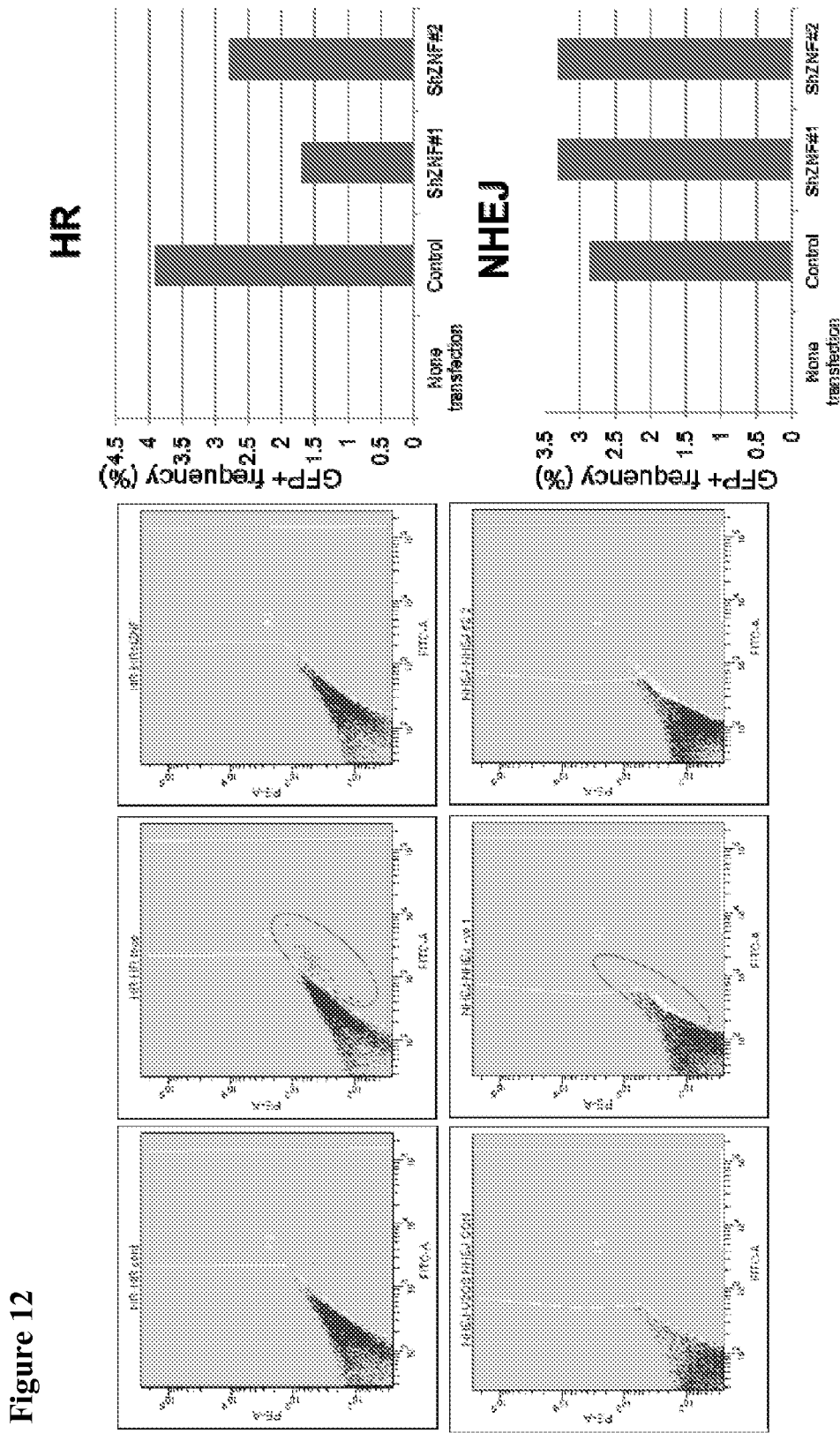
FIG. 12 shows the frequency of HR- and NHEJ-mediated DNA repair events in U2OS DR-GFP cells infected with independent shRNAs targeting ZNF365.

In addition, knockdown of ZNF365 impairs homologous recombination (HR)-mediated DNA repair as assessed by analyzing the frequency of HR- and NHEJ-mediated DNA repair events in U2OS DR-GFP cells infected with independent shRNAs targeting ZNF365 (FIG. 12). Each value shown in FIG. 12 corresponds to the percentage of HR relative to the control and represents the mean of three independent experiments. By contrast, ZNF365 knockdown enhances NHEJ-dependent repair efficiency.

Figure 13:
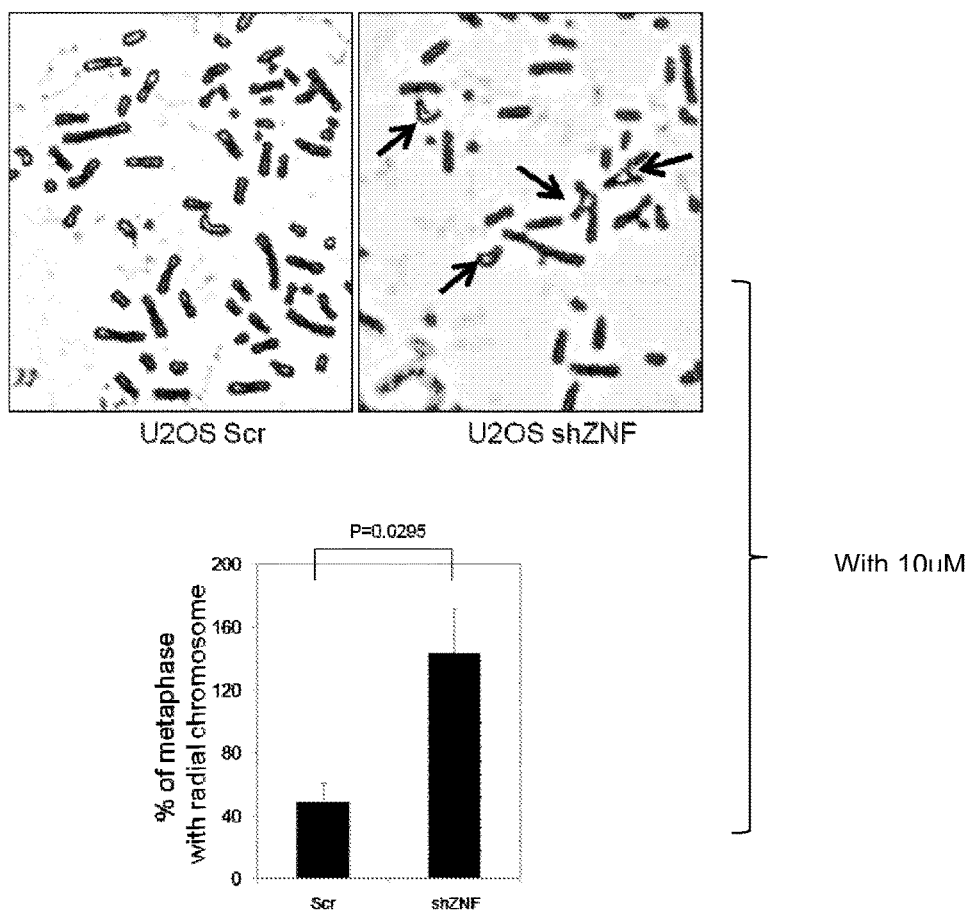
FIG. 13 shows representative images and quantification of radial structures of metaphase chromosomes from U2OS control and shZNF365 cells treated for 48 hrs with ABT888 (10 µM).

ZNF365 knockdown also affects chromosomal structural. FIG. 13 shows representative images and quantification of radial structures of metaphase chromosomes from U2OS control and shZNF365 cells treated for 48 hrs with ABT888 (10 µM). At least 100 metaphase were counted for each cell type to calculate the mean radial structures distribution resulting in a p-value of 0.0295 using a two tail Student's t-test.

Figure 14:
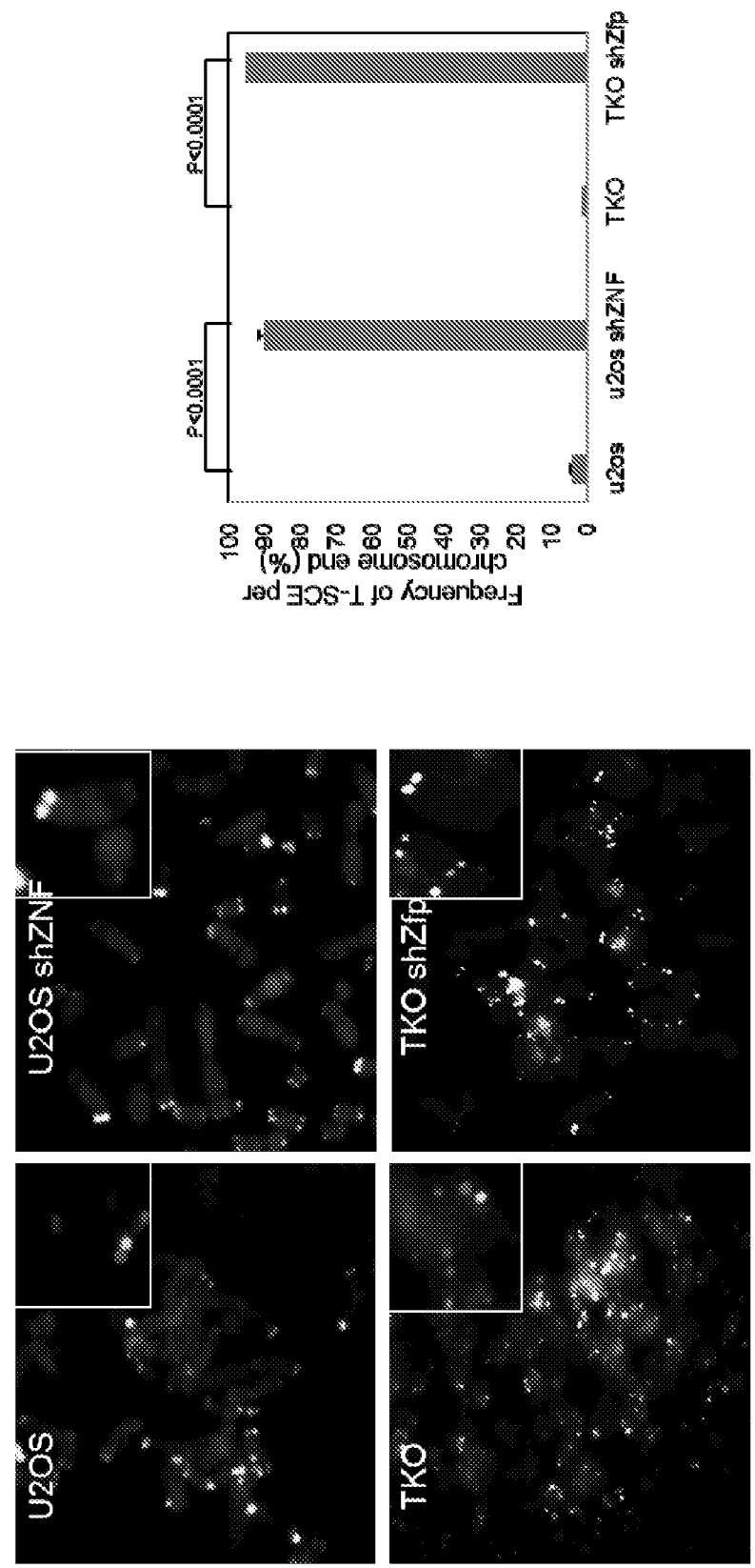
FIG. 14 shows representative CO-FISH images and quantification of cells at metaphases hybridized with probes against the leading (Tel-G, red) and lagging (Tel-C, green) telomere.

In addition, ZNF365 knockdown increased the number of telomere sister chromatid exchange (SCE) events. FIG. 14 shows representative CO-FISH images and quantification of cells at metaphases hybridized with probes against the leading (Tel-G, red) and lagging (Tel-C, green) telomere. U2OS wild-type chromosomes show two telomeric signals of each color per chromosome, whereas ZNF365 or Zfp365 shRNA knocking down cells show chromosomes where signals are interchanged at both sister telomeres (yellow). Quantification of total SCE (T-SCE) in U2OS wild-type cells versus shRNA knockdown cells indicated that T-SCE increased significantly in the ZNF365 and shZfp365 knockdown cells compared with wild-type cells (FIG. 14; t-test, P<0.0001, respectively). The numbers above the bars in FIG. 14 represent total T-SCE events out of the total number of chromosomes counted.

Figure 15:
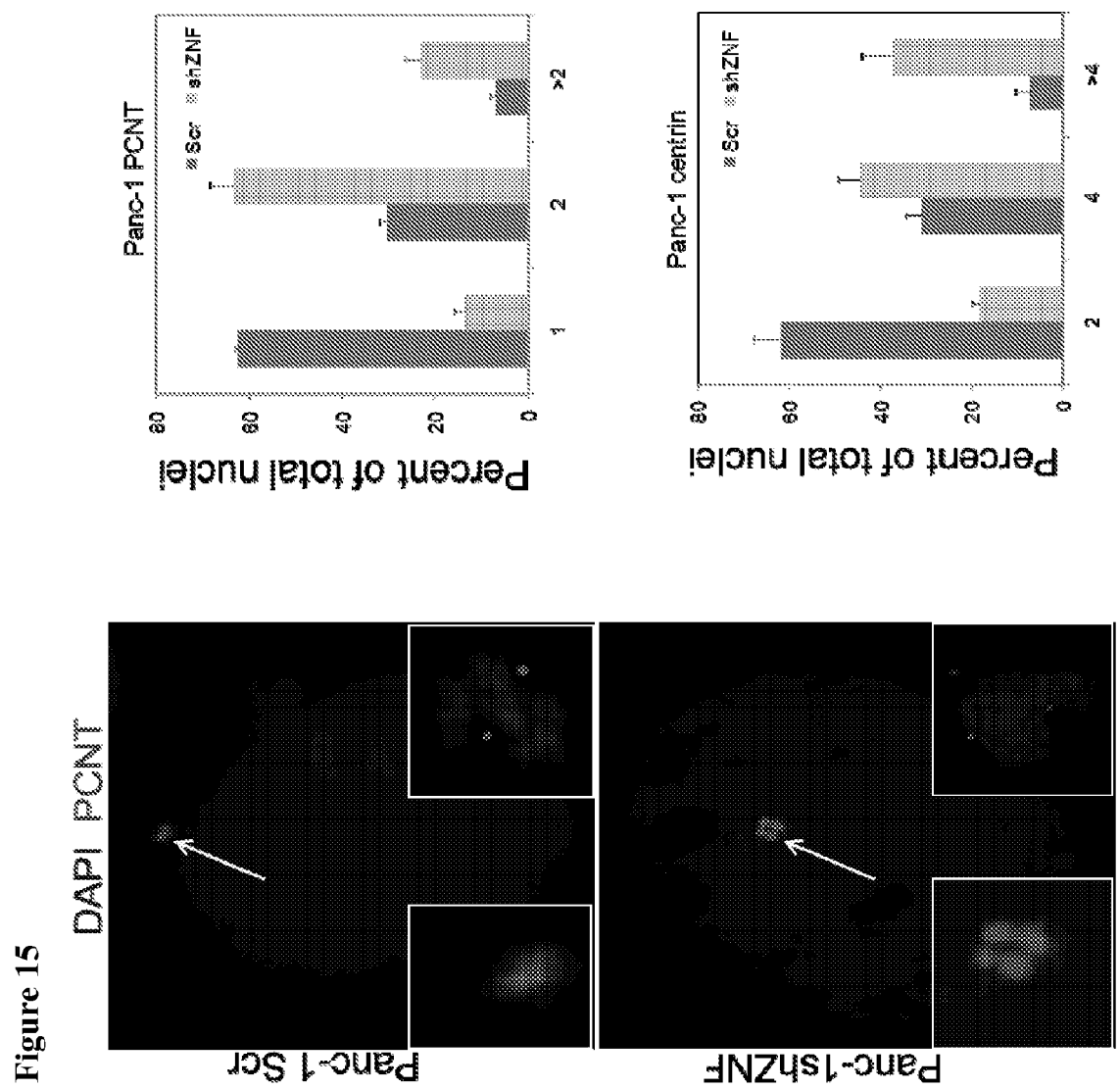
FIG. 15 shows representative images and quantification of pericentrin (PCNT) staining in Panc-1 cells treated with control scrambled shRNA (Scr) or shRNA targeting ZNF365 (shZNF).

Finally, knockdown of ZNF365 induces abnormal duplication of centrosomes and centrioles. FIG. 15 shows representative images and quantification of pericentrin (PCNT) staining in Panc-1 cells treated with control scrambled shRNA (Scr) or shRNA targeting ZNF365 (shZNF), wherein the arrows point to PCNT-positive centrosomes and the insets show higher magnification of centrosomes (bottom left) and multiploar metaphase (bottom right). For quantification purposes, abnormal centrosome and centriole numbers in Panc-1 scr and shZNF cells by pericentrim and centrin staining, respectively, wherein centrosome numbers (1, 2 or >2) and centriole numbers (2, 4 or >4) were counted. Each bar shown in FIG. 15 indicates the average±standard deviation of at least 3 independent counts of at least 50 cells.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting the proliferation of breast cancer cells having less than a diploid copy number of ZNF365 in a human subject, the method comprising administering an inhibitor of PARP-1 and/or PARP-2 to a human subject determined to have less than a diploid copy number of ZNF365 n breast cancer cells, wherein the determination is achieved by:
    a) measuring the copy number of ZNF365 in a test sample comprising breast cancer cells; and
    b) determining that a less than diploid copy number of ZNF365 is present in the breast cancer cells in the test sample.

2. The method of claim 1, wherein ZNF365 encodes a protein that reduces DNA repair activity.

3. The method of claim 2, wherein the DNA repair activity is selected from the group consisting of non-homologous end joining, homologous recombination, and DNA single-strand break repair.

4. The method of claim 2, wherein the protein encoded by ZNF365 interacts with a protein selected from the group consisting of PARP-1, PARP-2, DNA-PK, Ku70, MRE11, RPA, CHEK1, and a topoisomerase.

5. The method of claim 1, wherein ZNF365 encodes a protein having an amino acid sequence selected from the group consisting of SEQ ID NOs: 2, 4, 6, and 8.

6. The method of claim 1, wherein the breast cancer cells harbor defects in genes encoding proteins mediating non-homologous end joining, homologous recombination, or DNA single-strand break repair.

7. The method of claim 6, wherein the breast cancer cells harbor defects in BRCA1, BRCA2, and/or Fanconi anemia (FANC) genes.

8. The method of claim 1, further administering chemotherapy, radiation therapy, or a combination of chemotherapy and radiation therapy, wherein said chemotherapy does not target PARP-1 and/or PARP-2.

9. The method of claim 8, wherein the chemotherapy comprises inhibitors selected from the group consisting of inhibitors of DNA-PK, Ku70, MRE11, RPA, CHEK1, and topoisomerases.

* * * * *